US005858687A

United States Patent [19]

Manger et al.

[11] Patent Number: 5,858,687

[45] Date of Patent: Jan. 12, 1999

[54] CELL BIOASSAY OF NEUROTOXINS

[75] Inventors: Ronald L. Manger, Edmonds; Linda S. Leja, Everett; Sue Y. Lee, Kent; James M. Hungerford, Bothell; Marleen M. Wekell, Redmond, all of Wash.

[73] Assignee: The United States of America as represented by the Department of Health and Human Services, Washington, D.C.

[21] Appl. No.: 450,877

[22] Filed: May 26, 1995

Related U.S. Application Data

[63] Continuation-in-part of Ser. No. 45,067, Apr. 12, 1993, Pat. No. 5,420,011.

[51] Int. Cl.[6] .................................................. G01N 33/567

[52] U.S. Cl. .......................... 435/7.21; 435/26; 435/948; 436/501; 436/815

[58] Field of Search ........................... 435/7.21, 21, 948, 435/975, 26; 436/501, 815

[56] References Cited

U.S. PATENT DOCUMENTS 5,118,624 6/1992 Parrish et al. .

OTHER PUBLICATIONS

Hungerford et al., "Analytical Methods for Marine Toxins", *Handbook of Natural Toxins,* vol. 7, Food Poisoning, Tu, ed., pp. 416–473, Marcel Decker, Inc., New York (1992).

Catterall, "The Voltage Sensitive Sodium Channel: A Receptor for Multiple Neurotoxins", *Toxic Dinoflagellates,* Anderson et al., eds., pp. 329–342, Elsevier, New York (1985).

Yasumoto et al., "A Survey of Comparative Toxicity in the Food Chain of Ciguatera", *Bull. Jap. Soc. Sci. Fish.* 43(8): 1015–1019 (1977).

Scudiero et al., "Evaluation of a Soluble Tetrazolium/Formazan Assay for Cell Growth and Drug Sensitivity in Culture Using Human and Other Tumor Cell Lines", *Cancer Res.* 48:4827–4833 (1988).

Paull et al., "The Synthesis of XTT", *J. Heterocyclic Chem.* 25: 911–913 (1988).

Gallacher et al., "A Tissue Culture Assay for Direct Detection of Sodium Channel Blocking Toxins in Bacterial Culture Supernates", *FEMS Microbiology Letters* 92: 101–108 (1992).

Hungerford, James M., "Seafood Toxins and Seafood Products", *76 General Referee Reports: Journal of AOAC International* 120–128 (1993).

Catterall, William A., Neurotoxins that Act on Voltage–Sensitive Sodium Channels in Excitable Membranes, *20 Ann. Rev. Pharmacol. Toxicol.* 15–43 (1980).

Davis, Charles C., "Gymnodinium Brevis Sp. Nov., a Cause of Discolored Water and Animal Mortality in the Gulf of Mexico", *Botanical Gazette* 358–360 (1948).

Steidinger, Karen A. and Daniel G. Baden, "Toxic Marine Dinoflagellates", Dinoflagellates, (1984).

Baden, Daniel G., "Marine Food–Borne Dinoflagellate Toxins", 82 *Intl. Review of Cytology* (1983).

Bidard et al., "Ciguatoxin is a Novel Type of $Na^+$ Channel Toxin", 259 *The Journal of Biological Chemistry* 8353–8357 (1984).

Kogure et al., "A Tissue Culture Assay for Tetrodotoxin, Saxitoxin and Related Toxins" 26 *Toxicon* 191–197 (1988).

Jellett et al., "Paralytic Shellfish Poison (Saxitoxin Family) Bioassays: Automated Endpoint Determination and Standardization of the in vitro . . . ", 30 *Toxicon* 1143–1156 (1992).

Mosman, Tim, "Rapid Colorimetric Assay for Cellular Growth and Survival: Application to Proliferation and Cytotoxicity Assays", 65 *Journal of Immunological Methods* 55–63 (1983).

"Paralytic Shellfish Poison: Biological Method, Final Action" 959.08 *AOAC Official Methods of Analysis* 881 (1990).

Carmichael, James, "Evaluation of a Tetrazolium–based Semiautomated Colorimetric Assay: Assessment of Chemisensitivity Testing", 47 *Cancer Research* 936–942 (1987).

Catteral, William A., and Martin Risk, "Toxin $T_{46}$ from *Ptychodiscus brevis* (formerly *Gymnodinium breve*) Enhances Activation . . . ", 19 *Molecular Pharmacology* 345–348 (1981).

Kotnik, Vladimir, and W. Robert Fleischmann, Jr., "A Simple and Rapid Method to Determine Hemotopoietic Growth Factor Activity", 129 *Journal of Immunological Methods* 23–30 (1990).

Wasserman, Todd H. and Peter Twentyman, "Use of a Colorimetric Microtiter (MTT) Assay in Determining the Radiosensitivity of Cells from Murine Solid Tumors", 15 *Int. J. Radiation Oncology Biol. Phys.* 699–702 (1988).

(List continued on next page.)

*Primary Examiner*—Patricia Duffy
*Attorney, Agent, or Firm*—Fitch, Even, Tabin & Flannery

[57] ABSTRACT

A cell bioassay is provided for determining the presence in a fluid sample of a sodium channel-activating toxin wherein (a) a fluid sample is incubated in the presence of a culture of cells which express voltage-gated sodium channels and which are responsive in a dose-dependent manner to sodium channel-activating toxins and a medium comprising an agent which causes persistent activation of the voltage-gated sodium channel; (b) the culture is incubated with a medium comprising an indicator which is acted upon by living cells to generate a discernable result, (c) the culture is observed for an incidence of the result, and an observation of the result is correlated with the presence of the toxin in the sample. A simplified assay where steps (a) and (b) are effected together also is provided, as is a cell bioassay for determining the sodium channel affect of a toxin in a fluid sample. A competitive assay for sodium channel-blocking toxins also is provided wherein the fluid sample and culture of cells are incubated with a medium comprising (i) an agent which causes persistent activation of the voltage-gated sodium channel and (ii) a sodium channel-activating toxin. Kits for performing the assays also are provided.

16 Claims, 10 Drawing Sheets

OTHER PUBLICATIONS

Alley et al., "Feasibility of Drug Screening with Panels of Human Tumor Cell Lines Using a Microculture Tetrazolium Assay", 48 *Cancer Research* 589–601 (1988).

Pearson et al., "Combined Drug and Immunotoxin Therapy Against a Human Colon Tumor Xenografted into Nude Mice", 30 *Proc. of the Amer. Assoc. for Cancer Research* (1989).

Manger et al., "Detection of Ciguatoxin, Brevetoxin, and Saxitoxin by Cell Bioassay", *Intl. Workshop on Ciguatera Management* Bribie Island, Australia (1993).

Manger et al., "Tetrazolium–Based Cell Bioassay for Neurotoxins Active on Voltage–Sensitive Sodium Channels: Semiautomated Assay for Saxitoxins, Brevetoxins, and Ciguatoxins", *Anal. Biochem.* 214: 190–194 (1993).

Manger et al., "Cell Bioassay for Sodium Channel Effectors", *Sixth Intl Conference on Toxic Marine Phytoplankton* Nantes, France, 127 (1993).

Manger et al., "Detection of Sodium Channel Effectors", *AOAC Intl Meeting and Exposition* Washington, DC, (1993).

Manger et al., "Assessment of Marine Toxins by Cell Bioassay", *New Developments in Seaford Science and Technology* Vancouver, Canada, 22 (1994).

Manger et al., "In vitro Analysis of Ciguatoxins, Brevetoxins, and Saxitoxins", *Intl. Symp. on Ciguatera and Marine Natural Products* South Kohala, Hawaii (1994).

Manger et al., "Analysis of Ciguatoxins, Brevetoxins, Saxitoxins, and Seafood Extracts by Cell Bioassay", *VIIIth Intl. Symp. on Toxic Microorganisms* Peoria, Illinois (1994).

Manger et al., "Detection of Sodium Channel Toxins: Directed Cytotoxicity Assays of Purified Ciguatoxins, Brevetoxins, Saxitoxins, and Seafood Extracts", *J. AOAC Intl.* 78(2): 521–527 (1995).

Manger et al., "Comparative Response of Human and Murine Cell Lines by Cell Bioassay to Sodium Channel . . . ", *Fifth Pan Amer. Symp. on Animal, Plant, and Microbial Toxins* Frederick, Maryland (1995).

Bonora et al, Curr. Microbiol, 1982, 7/4 (217–221).

- ■— STX +PbTx-1 (6 ng)
- □— STX -PbTx-1 (6 ng)

6ng PBTX-1

X-axis: STX (ng), $10^{-4}$ to $10^2$
Y-axis: PERCENT OF CONTROL (7 HR)

CELL BIOASSAY OF NEUROTOXINS

This application claims the benefits of priority under 35 USC § 120 which is a continuation in part of U.S. Application Ser. No. 08/045,067, filed Apr. 12, 1993 now U.S. Pat. No. 5,420,011 issued May 30, 1993.

BACKGROUND OF THE INVENTION

The present invention relates to an assay for the detection of sodium channel-affecting toxins, particularly marine toxins, based upon mitochondrial dehydrogenase activity in the presence of ouabain and veratridine. More specifically, the present invention concerns a cell bioassay that allows the detection of either sodium channel-blocking toxins, such as saxitoxin, or sodium channel-activating toxins, such as brevetoxin or ciguatoxin.

Commercially important species of shellfish and finfish are known to occasionally present a serious health risk to consumers due to the presence of accumulated marine toxins. A significant number of these marine toxins exert their effects by interaction with voltage-sensitive sodium channels in excitable membranes. These toxins may be sodium channel-blocking toxins or sodium channel-activating toxins. For example, paralytic shellfish poisoning (PSP) is attributed to the ingestion of molluscan shellfish that have accumulated saxitoxins, which selectively block ion transport at the sodium channel, or related compounds from toxic dinoflagellate blooms. Neurotoxic shellfish poisoning (NSP) is caused by the ingestion of shellfish that have sequestered brevetoxins from the dinoflagellate associated with Florida's red tide. Brevetoxins perturb normal membrane properties of excitable cells by activating sodium channels. Another class of marine neurotoxins, ciguatoxins, a group of structurally related polyethers which accumulate in tropical fish, exert their biological effects through the activation of the sodium channel.

Monitoring programs for marine toxins have depended in large part upon mouse bioassays. Although mouse bioassays have for many years provided a fairly reliable assessment of risk, there is mounting pressure to develop alternative assays to reduce the reliance on animal testing. To this end, Kogure et al. developed a tissue culture assay for sodium channel-blocking toxins such as tetrodotoxin and saxitoxin. Kogure et al., *Toxicon* 26 (2): 191–97 (1988). In the Kogure assay, a mouse neuroblastoma cell line (Neuro-2a) is treated with a fixed concentration of the sodium channel-activator veratridine in the presence of ouabain, an inhibitor of Na+/K+ ATPase. The combined effect of these agents is an enhanced sodium influx, leading to altered cell morphology, subsequent decrease in cell viability and ultimate cell lysis. Tetrodotoxin, saxitoxin and related toxins which block sodium channels antagonize this effect, essentially "rescuing" the cells in a dose-dependent manner. This phenomenon provides the basis of a sensitive in vitro bioassay for these toxins. Evaluation of the Kogure assay requires the visual scoring of 200 or more cells per sample or well, which makes this assay a potentially time-consuming and operator-dependent task.

Scoring of this assay was improved by the modifications described by Jellett et al., *Toxicon*, 30 (10): 1143–56 (1992), the contents of which are hereby incorporated by reference. Jellett et al. used a microplate reader for automated determinations of absorbances of toxin-treated cells which were stained with crystal violet. This assay exploits the difference in adherence to the culture well of cells treated only with ouabain/veratridine and PSP toxin-treated cells. The former cells exhibit diminished adherence to the culture well, associated with swelling and lysis, and are readily removed by rinsing, whereas the latter cells which are protected from the effects of ouabain/veratridine, retain substrate adherence. Thus, cells affected only by ouabain/veratridine lose adherence and are removed during rinsing, while cells inoculated with the toxin remain in the well.

In the Jellett assay, wells containing Neuro-2a cells are inoculated with toxin and then with ouabain/veratridine, incubated, and subsequently rinsed. After rinsing, the wells are fixed and stained with crystal violet. The processed plates are then dried, and the stained cells are digested in acetic acid. Finally, the plates are read for absorbance of crystal violet in each well, with the absorbance being directly related to the amount of PSP toxin originally present. While these modifications notably improve the cell bioassay of Kogure et al., the assay still requires numerous steps and involves the mechanical removal of cells and treatment of the plates which are subject to operator variability.

There is a need, therefore, for a simplified bioassay for detecting sodium channel-blocking toxins. There also is a need for a tissue culture-based bioassay which can detect sodium channel-activating toxins. There also is a need for a tissue culture-based bioassay that is amenable to detecting both sodium channel-blocking and sodium channel-activating toxins, as well as an assay for determining the sodium channel affect of a toxin.

SUMMARY OF THE INVENTION

It is therefore an object of the present invention to provide an improved cell bioassay for sodium channel-affecting toxins.

A further object of the present invention is to provide a simplified cell bioassay for sodium channel affecting toxins.

Yet another object of the present invention is to provide a kit for carrying out the improved cell bioassay.

In accomplishing the foregoing objectives, there has been provided, in accordance with one aspect of the present invention, a cell bioassay method for determining the presence in a fluid sample of a toxin having sodium channel-activating activity which comprises the steps of: (a) incubating, in the presence of a portion of the fluid sample, a culture of cells which express voltage-gated sodium channels and which are responsive in a dose-dependent manner to sodium channel-activating toxins with a medium comprising an agent which causes persistent activation of the voltage-gated sodium channel; (b) incubating the culture with a medium comprising an indicator which is acted upon by living cells to generate a discernable result, and (c) observing the culture for an incidence of the result, whereby an observation of the result is correlated with the presence of the toxin in the sample. A simplified assay wherein steps (a) and (b) are effected together also is provided.

In accordance with another aspect of the present invention there is provided a kit for use in the foregoing cell bioassay method which comprises, in packaged combination (a) a first container containing a culture of cells which express voltage-gated sodium channels and which are responsive in a dose-dependent manner to sodium channel-activating toxins, (b) a second container containing a medium comprising a solution of an agent which causes persistent activation of the voltage-gated sodium channel and an indicator which is acted upon by living cells to generate a discernable result, or (b') a second container containing a medium comprising a solution of an agent which causes persistent activation of the voltage-gated sodium channel and a third container containing an indicator which is acted upon by living cells to generate a discernable result, and (c) a separate container containing a known amount of the toxin.

In accordance with another aspect of the invention, a cell bioassay for determining the sodium channel affect of a toxin in a fluid sample is provided, comprising the steps of (a) incubating a plurality of cultures of cells which express voltage-gated sodium channels and which are responsive in a dose-dependent manner to sodium channel-affecting toxins with (i) a medium comprising an agent which causes persistent activation of the voltage-gated sodium channel, and (ii) a portion of the fluid sample, each of the cultures being incubated with a different concentration of fluid sample, (b) incubating the cultures with a medium comprising an indicator which is acted upon by living cells to generate a discernable result, and (c) observing the cultures for an incidence of the result, wherein the presence of a sodium channel-blocking toxin is indicated by an increase in the discernable result observed in step (c) as the concentration of fluid sample increases and the presence of a sodium channel-activating toxin is indicated by a decrease in the discernable result observed in step (c) as the concentration of fluid sample increases. The independence of the result on the presence of an agent which causes persistent activation of the voltage-gated sodium channel indicates the presence of a toxin that is not sodium channel-affecting.

In accordance with yet another aspect of the present invention, a competitive cell bioassay for determining the presence in a fluid sample of a toxin having sodium channel-blocking activity is provided, which method comprises the steps of (a) incubating, in the presence of a portion of the fluid sample, a culture of cells which express voltage-gated sodium channels and which are responsive in a dose-dependent manner to sodium channel-activating toxins with a medium comprising (i) an agent which causes persistent activation of the voltage-gated sodium channel and (ii) a sodium channel-activating toxin; (b) incubating the culture with a medium comprising an indicator which is acted upon by living cells to generate a discernable result, and (c) observing the culture for an incidence of the result, whereby an observation of the result is correlated with the presence of the sodium channel-blocking toxin in the sample. A simplified assay wherein steps (a) and (b) are effected together also is provided.

In accordance with another aspect of the present invention there is provided a kit for use in the foregoing competitive cell bioassay method which comprises, in packaged combination (a) a first container containing a culture of cells which express voltage-gated sodium channels and which are responsive in a dose-dependent manner to sodium channel-activating toxins, (b) a second container containing a known amount of a sodium-channel activating toxin, and (c) a third container containing a medium comprising a solution of an agent which causes persistent activation of the voltage-gated sodium channel and an indicator which is acted upon by living cells to generate a discernable result, or (c') a third container containing a medium comprising a solution of an agent which causes persistent activation of the voltage-gated sodium channel and a fourth container containing an indicator which is acted upon by living cells to generate a discernable result, and (d) a separate container containing a known amount of the sodium-channel blocking toxin.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWING

The present invention is more readily understood by reference to the accompanying drawing by which.

DETAILED DESCRIPTION OF THE PREFERRED EMBODIMENTS

Figure 1:
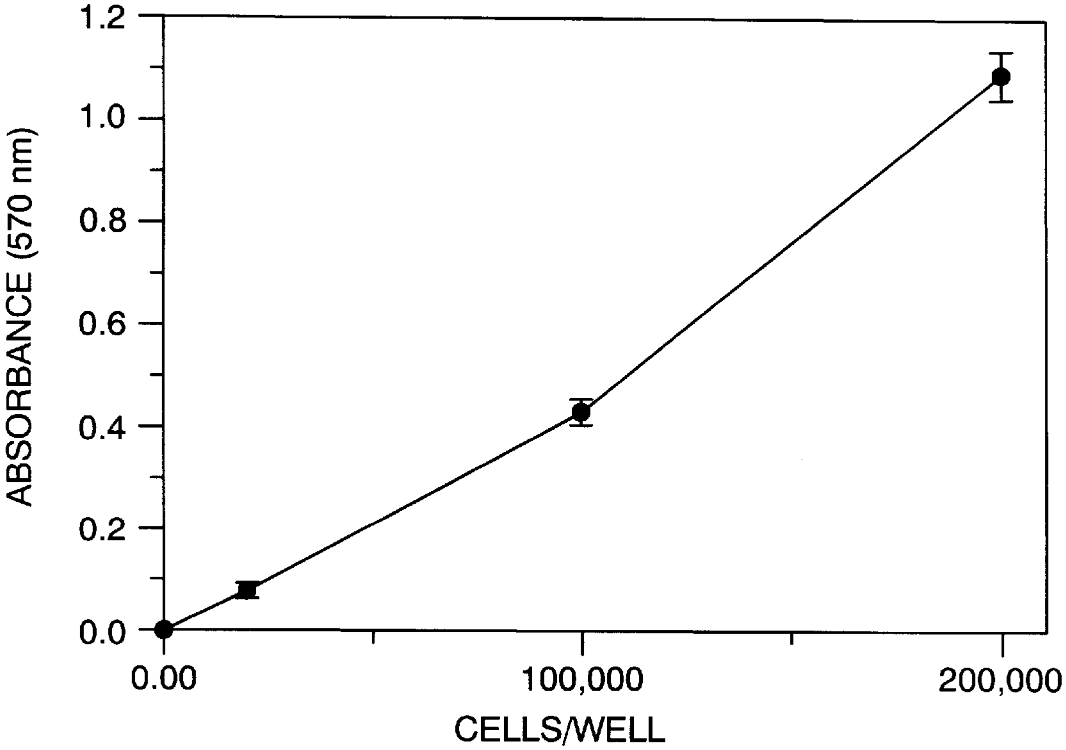
FIG. 1 is a graph of absorbance as a function of cell number in the inventive bioassay.

The present cell assay determines the presence of sodium channel-affecting toxins based on their bioactivity. This is in contrast to virtually all other detection methods (HPLC, mass spectroscopy, immunoassay), with the exception of animal testing, which detect physical or chemical parameters, which may or may not correlate with the actual potency or biological effect of the toxin. The present cell bioassay directly measures the toxin's effect (or potency) in a biological system and thus is similar to animal toxicity testing. Moreover, the present cell bioassay is 10,000 to 100,000 fold more sensitive than the standard mouse bioassay, is easier to run, and does not present potential ethical problems. The cell bioassay can be used as both a qualitative and quantitative screening method to insure the quality and safety of finfish derived from commercial fisheries worldwide. Potential applications also include forensic testing to determine the presence and amount of toxin in patient body fluids such as sera, and the examination of processed seafood products believed to be adulterated with toxic finfish.

The cell bioassay according to the present invention represents a significant improvement over the known assay methods. The inventive bioassay is simpler, faster and more sensitive than the standard mouse assay, and requires less sample than the mouse assay. Furthermore, the instant bioassay also can be carried out more easily than other previously known tissue-based assays because it requires fewer steps and no intermediate washing or fixation steps.

It is contemplated that a bioassay according to the invention has utility in determining the presence, not only of marine toxins, but also of any other similarly acting sodium channel-affecting toxins. (As used herein, the term "sodium channel-affecting" toxins denotes both sodium channel-blocking toxins and sodium channel-activating toxins.) Exemplary toxins whose presence can be determined by use of bioassays within the invention include: carbamate toxins such as saxitoxin (STX), neosaxitoxin (NEO), gonyautoxins (GTX-I, GTX-II, GTX-III, GTX-IV); other members of the saxitoxin, neosaxitoxin and gonyautoxin families such as decarbamoyl (dc) toxins, including dc-STX, dc-NEO, dc-GTX-I, etc.; N-sulfocarbamoyl toxins such as toxins B-1, B-2, C-1, C-2, C-3 and C-4; tetrodotoxins; other PSP-producing toxins; brevetoxins such as PbTx-1, PbTx-2, PbTx-3, PbTx-5, PbTx-6, PbTx-7, PbTx-8, etc.; ciguatoxins such as CTX-1, CTX-2, CTX-3, etc.; other NSP-producing toxins; and the like (see J. Hungerford et al., in *Handbook of Natural Toxins*, pp. 415–473, A. Tu, ed., Marcel Dekker Inc, (New York, 1992)).

Unlike conventional assay methods, a bioassay within the present invention is effective in determining the presence of toxins having either sodium channel-activating (or enhancing) activity or sodium channel-blocking activity. The inventive bioassay thus has additional utility as a diagnostic tool for determining the sodium channel affect of a toxin. Specifically, the reduction of cytotoxicity ("cell rescue") in the presence of an agent which causes persistent activation of the voltage-gated sodium channel is indicative of a sodium channel-blocking toxin, such as saxitoxin or tetrodotoxin, the enhancement of cytotoxicity in the presence of such an agent is indicative of a sodium channel-activating toxin, such as a brevetoxin or ciguatoxin, and no effect on cytotoxicity in the presence of such an agent, or cytotoxicity in the absence of such an agent, is indicative of a toxin other than a sodium channel-affecting toxin, such as a diarrhetic shellfish poisoning (DSP) toxin, e.g., okadaic acid.

The cell cultures employed according to the inventive bioassay express voltage-gated sodium channels which are the specific subcellular targets of the toxins detected by the present invention. Voltage-gated sodium channels are expressed primarily upon nerve, heart and skeletal muscle cells (Catterall, *Ann. Rev. Pharmacol. Toxicol.* 20: 15–43, (1980) and *Toxic Dinoflagellates* p. 329–342, (1985)). As disclosed in Caterall, supra, cells can be screened for the expression of voltage-gated sodium channels by using radiolabeled neurotoxin and assessing the binding of the neurotoxin to the cell. Saturable binding is an indication of significant levels of voltage-gated sodium channels, and thus that the cells are suitable for use in the present assay.

The cells also are responsive in a dose-dependent manner to sodium channel-affecting toxins. The dose-dependent response of the cells occurs in the context of prior exposure to an agent which causes persistent activation of the voltage-gated sodium channel, such as the ouabain/veratridine system. Other agents which cause persistent activation of the voltage-gated sodium channel include aconitine, batrachotoxin, and grayanotoxin, as described in Catterall, supra.

While Kogure et al. *Toxicon* 26(2): 191–197 (1988) found that veratridine alone did not induce a significant morphological change, applicants have found, surprisingly, that veratridine alone can be used as the agent. FIGS. 6A, 6B, 7A and 7B show results achieved with veratridine as the agent which causes persistent activation of the voltage-gated sodium channel. The use of veratridine alone is not preferred, however, because of the poorer sensitivity and/or longer time needed to perform the assay. (See FIGS. 6A and 6B.)

Figure 7A:
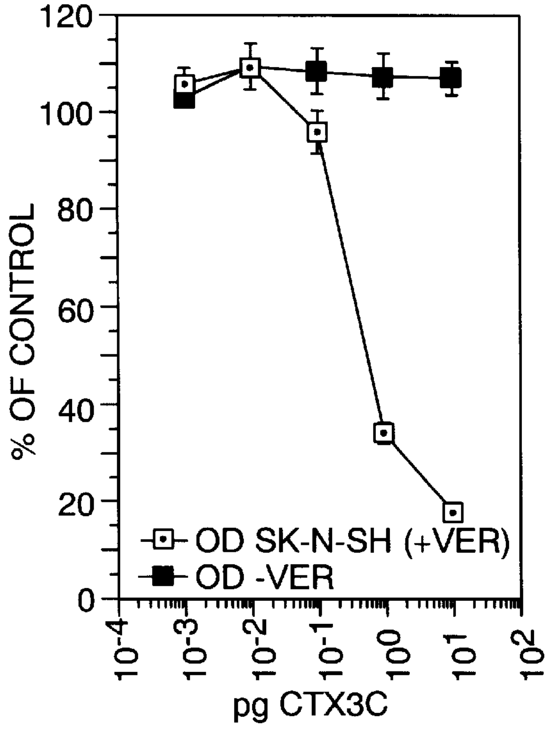
FIG. 7A shows human neuroblastoma SK-N-SH cells vs. ciguatoxin (CTX3C) in the presence (⊡) or absence (■) of veratridine.
Figure 7B:
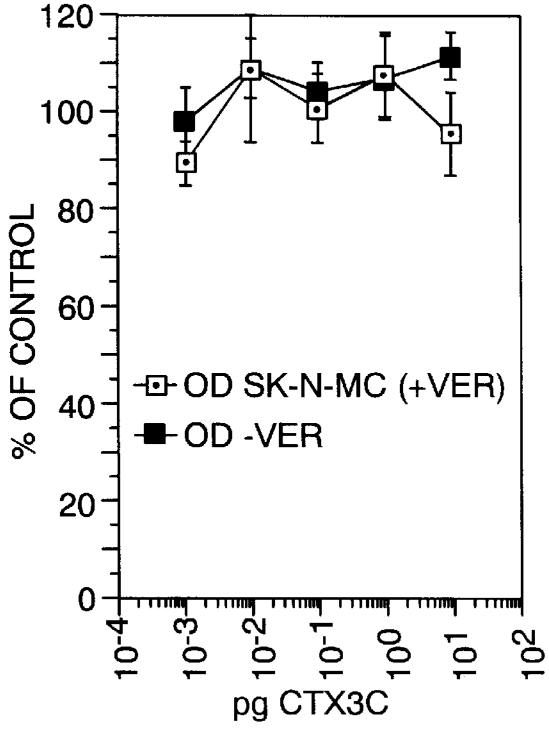
FIG. 7B shows human neuroblastoma SK-N-MC cells vs. ciguatoxin (CTX3C) in the presence (⊡) or absence (■) of veratridine.

The efficacy of veratridine alone appears to be cell-line dependent. For example, Neuro 2A cells and human neuroblastoma SK-N-SH cells responded appropriately to veratridine alone (FIGS. 6B and 7A) while human neuroblastoma SK-N-MC cells did not (FIG. 7B). One can readily determine whether a cell line will respond in a dose-dependant manner with a toxin in the presence of veratridine alone by measuring the cytotoxicity of the cells in the presence of the toxin with and without veratridine, as done, for example, in FIGS. 6A, 6B, 7A and 7B.

The cells should be readily cultured, and should begin to show a response within a reasonable time, such as about 4 to 18 hours in the case of sodium channel-activating toxins, or about 24 to 48 hours in the case of sodium channel-blocking toxins.

Suitable cell lines include mouse and human neuroblastoma cells, rat adrenal pheochromatoma cells, and human rhabdomyosarcoma cells. Preferred cells include mouse neuroblastomas of the cell line Neuro-2a (ATCC CCL 131) and human neuroblastomas of the cell lines SK-N-SH (ATCC HTB-11) and SK-N-MC (ATCC HTB-10). While human neuroblastoma cells are more sensitive to the ouabain/veratridine system than mouse neuroblastoma cells, with the human cells showing 30–50% toxicity in 7 hours and the mouse cells show only 15% toxicity in 7 hours, this sensitivity does not interfere with the present assay.

The cells must also be responsive to the selected indicator. The indicator employed in a bioassay within the instant invention distinguishes active, living cells from dead cells, and is a substrate for mitochondrial dehydrogenase. Living cells act upon the indicator to produce a measurable product, while dead cells do not act upon the indicator to produce a measurable product. Preferred indicators include 3-(4,5-dimethylthiazol-2-yl)-2,5-diphenyl tetrazolium bromide (MTT), 2,3-bis(2-methoxy-4-nitro-5-sulfophenyl)-2H-tetrazolium-5-carboxanilide inner salt (XTT) (Sigma #X4251) (Parsons et al., *J. Heterocyclic Chem.* 25: 911 (1988); Scudievo et al., *Cancer Res.* 48: 4827 (1988)) and methylene blue. MTT is metabolized only in living cells, whose mitochondria cleave its tetrazolium ring to produce a blue-colored formazan product. XTT is metabolized only in living cells, whose mitochondria cleave its tetrazolium ring to produce an orange/red formazan product. Methylene blue is decolorized by living cells by cell dehydrogenase activity.

In one embodiment of the present invention, the assay is performed by (a) incubating, in the presence of a portion of the sample to be assayed, a culture of cells which express voltage-gated sodium channels and which are responsive in a dose-dependent manner to sodium channel-activating toxins with a medium comprising an agent which causes persistent activation of the voltage-gated sodium channel; (b) incubating the culture with a medium comprising an indicator which is acted upon by living cells to generate a discernable result, and (c) observing the culture for an incidence of the result, whereby an observation of the result is correlated with the presence of the toxin in the sample. No intermediate washing or fixing steps are required in the inventive bioassay method.

In a preferred embodiment, steps (a) and (b) are effected together, such that the indicator is contained in the same medium, resulting in a very simple assay that can be performed, for example, in test tubes. In this embodiment, the cells, agent and indicator are placed in the same medium for incubation. The medium may be a matrix which holds viable cells in a semi-solid suspension, such as agar, aragose, methyl cellulose, gelatin and coagulated plasma. XTT and methylene blue are preferred indicators because they form a detectable product that does not need an additional solvent (whereas the MTT-formazan product needs a solvent such as DMSO) for colorimetric analysis. After the cells are incubated the tubes are read for color changes, and the color change is correlated to the amount of toxin present in the sample.

This embodiment incorporates features of previous cytotoxicity suspension assays (Arai et al., *J. Antibiot.*, A9:169–171 (1956) and Buskirk et al., *J.N.C.I.*, 51: 135–138 (1973)) into the cell bioassay described above. In particular, neuroblastoma cells are suspended in soft agar containing all required reagents including sample toxin and methylene blue. The ouabain/veratridine-dependent cytotoxicity produced by sodium channel-activating toxins should appear in this system as a decreased ability to decolorize methylene blue in comparison to appropriate controls.

For example, Neuro 2a cells are seeded into an agar suspension containing methylene blue and ouabain and veratridine, and incubated with the sample at 37° C. for 4 hours. The tubes are read visually or by a spectrophotometer, and the color is correlated with color of a culture comprising a known amount of toxin, thereby determining the presence and/or amount of toxin present.

In another embodiment, a plurality of cultures of cells are incubated with the medium and portions of the sample, where each culture is incubated with a different concentration of sample. This embodiment can be used to obtain a quantitative determination of the amount of toxin present in the sample.

For example, the dose-dependent response of the positive samples can be compared to the response of known toxin standards. The dilution of sample that produced a specified response (i.e., a 50% reduction in formazan production) would be correlated to the concentration of toxin standard that produced the same response (i.e., 50% reduction in formazan). This concentration is then corrected by multiplying by the dilution factor of the sample to derive the level of toxin in the original sample.

Another embodiment of the invention allows the determination of the sodium channel affect of the toxin. In this embodiment, the relationship between the discernable result and the concentration of sample is used to determine whether the toxin is sodium channel-blocking, sodium channel-activating, or neither. This assay is performed as follows: a plurality of cultures of cells which are responsive in a dose-dependent manner to sodium channel-affecting toxins are incubated with (i) a medium comprising an agent which causes persistent activation of the voltage-gated sodium channel; and (ii) a portion of the fluid sample, with each culture being incubated with a different concentration of the fluid sample. The cultures are then incubated with a medium comprising an indicator which is acted upon by living cells to generate a discernable result, and the cultures are observed for an incidence of the result. As discussed above, the presence of a sodium channel-blocking toxin is indicated by an increase in the discernable result as the concentration of the sample increases and the presence of a sodium channel-activating toxin is indicated by a decrease in the discernable result as the concentration of the fluid sample increases.

By incubating a culture of cells with only the sample (and not the agent which activates the sodium channel), the presence of toxins which are not sodium channel-affecting can be determined. If the discernable result is independent of the presence of the agent, the toxin is not sodium channel-affecting, whereas if the discernable result is dependent on the presence of the agent, the toxin is sodium channel-affecting.

In another embodiment of the present invention, sodium channel blocking toxins can be detected in a competitive assay. The ability of sodium channel-blocking toxins to antagonize the effects of ciguatoxin or brevetoxin has been demonstrated in a number of systems including action potentials in giant squid axons (Westerfield et al., *Am. J. Physiol.* 232: C23–C29 (1977)), inotropic response in both isolated guinea-pig and human atria (Miyahara et al., in *Mycotoxins and Phycotoxins*, Natori et al., eds., Elsevier Scientific Publishing Co., Inc. (New York, 1989), pp. 399–406; Lewis et al., *Toxicon* 30: 907–914 (1992)), and $^{22}Na^+$ influx in synaptosomes and neuroblastoma cells (Poli et al., *Mol. Pharmacol.* 30: 129–135 (1986); Bidard et al., *J. Biol. Chem.* 259: 8353–8357 (1984)). Applicants have determined that the effect of a sodium channel-activating toxin in the cell bioassay is antagonized in a dose-dependent manner with sodium channel-blocking toxins. Accordingly, sodium channel blocking toxins can be detected in a competitive assay with sodium channel-activating toxins in accordance with the present invention.

In this method, a culture of cells which express voltage-gated sodium channels and which are responsive in a dose-dependent manner to sodium channel-affecting toxins is incubated, in the presence of a portion of the fluid sample, with a medium comprising (i) an agent which causes persistent activation of the voltage-gated sodium channel and (ii) a sodium channel-activating toxin. The culture is then incubated with a medium comprising an indicator which is acted upon by living cells to generate a discernable result, and the culture is observed for an incidence of the result, whereby an observation of the result is correlated with the presence of the sodium channel-blocking toxin in the sample.

This competitive assay offers a distinct advantage over other assays for sodium-channel blocking toxins in that this assay has the same rapid kinetics as the assay for sodium channel-activating toxins, and the time required to perform the assay is reduced from 24–48 hours to only 4–8 hours.

The competitive assay may be performed according to the simplified method discussed above. That is, the cells, fluid sample, agent, sodium channel-activating toxin and indicator can be incubated together in a single test tube (or other suitable vessel), which is then read for an incidence of the result. When methylene blue is used as the indicator, the presence of a sodium channel-blocking toxin will be indicated by the decolorization of methylene blue.

The cell bioassay of the present invention has a high tolerance of impurities in the sample. Accordingly, samples can be prepared from the flesh of animals by simplified purification processes, such as the acetone-chloroform method of Kimura et al., *Toxicon* 20: 907–912 (1982), or even more simplified processes set forth in Example 8 below, and accurately assayed in accordance with the present invention. It also is possible to directly assay the initial acetone extract, or an initial extract prepared with methanol, and may even be possible to directly assay tissue fluids without any processing whatsoever. Thus, a distinct advantage of the present assay is the minimal sample preparation it requires.

The present assay also is tolerant of acetonitrile, a solvent typically used in HPLC. Thus, it may be possible to easily couple HPLC with the present assay to obtain complimentary chemical structure/biological activity information.

The present bioassay offers the advantage of significantly improved sensitivity in comparison to the standard mouse bioassay. The animal assay can detect saxitoxin to a lower limit of 40 μg/100 g tissue See Hungerford et al., 7 HANDBOOK OF NATURAL TOXINS, 416–73, Marcel Dekkar, Inc. (New York 1992). In contrast, the cell bioassay according to the present invention can routinely detect purified saxitoxin at a level of 0.1 ng/10 μl, which is the equivalent of 2 μg/100 g tissue. Under some conditions, with extended MTT development time, the observed limit of detection can be reduced to as low as 0.02 ng/10 μl (0.4 μg/100 g). This sensitivity is comparable to that obtained by Jellett et al., supra. The inventive cell assay also shows excellent correlation with the results obtained with the standard mouse bioassay for saxitoxin.

In a similar manner, the instant cell bioassay is more sensitive to the presence of brevetoxins and ciguatoxins than the mouse bioassay. The $ID_{50}$ (the dose that produces a 50% reduction in cell viability) for brevetoxins in mice is 0.01 mg/20 g animal, i.p. injection. See Hungerford et al., supra. This correlates to 0.1 mg/100 g tissue extract and is the equivalent of a 1 ng/10 μl sample in the instant cell bioassay. In the examples given below, brevetoxins are detected at levels of 0.25 ng/10 μl (Example 5; also FIGS. 4*a–b*).

Ciguatoxic extracts (utilized in Example 6, below) produced death in 20 g mice following injection of 50 mg in 1 ml within 2.5 hours (estimated toxicity score of about 0.3 mouse units per mg; bioassay results and sample generously provided by Dr. Yoshitsugi Hokama, University of Hawaii), and contained the estimated equivalent of 100 ng ciguatoxin (CTX-1). The sodium channel activity of this extract was readily detected in the instant cell bioassay at levels of less than $10^{-4}$ mouse units, corresponding to approximately 1 pg of CTX-1.

As an index of the comparative utility of the cell bioassay to detect and quantitate the presence of ciguatoxins in finfish, a panel of semi-purified extracts from the Caribbean region were analyzed. These extracts were suspended in 1% Tween-60 and had been previously characterized by mouse bioassay (Dickey et al., *Memoirs of the Queensland Museum*, 34: 481–488 (1994)). A comparison of cell bioassay data derived from both the $ID_{50}$ values at 7 hr and the $ID_{90}$ values at 22 hr is shown in Table 1. In general, mouse survival ranked in order of potency as determined by cell bioassay. Furthermore, the cell assay revealed apparent sodium channel-activating activity in a number of extracts which had not produced death in animals. This may reflect the significant improvement of cell assay sensitivity over the mouse bioassay. In all cases activity detected by cell assay was dependent upon the presence of ouabain/veratridine in agreement with the presence of ciguatoxin in these extracts (data not shown). The tabulated results were from three separate experimental runs. Variability was judged as small as evidenced by the narrow range of results for the positive control, PbTx-1, which was analyzed for each run (Table 1).

TABLE 1

| SAMPLE | $ID_{50}$[a] 7 HR | $ID_{90}$[a] 22 HR | MOUSE ASSAY[b] SURVIVAL (HRS) |
|---|---|---|---|
| *Cynoscion arenarius* 92-07-1 | ND | ND | >48, >48 |
| *Sphyrana barracuda* VI-13 | >40 | >40 | >48, >48 |
| *Sphyrana barracuda* VI-59 | >40 | >32 | >48, >48 |
| *Sphyrana barracuda* VI-63 | >40 | 22 | >48, >48 |
| *Carnax latus* VI-32 | >40 | 20 | >48, >48 |
| *Sphyrana barracuda* VI-81 | >40 | 9 | >48, >48 |
| *Sphyrana barracuda* VI-54 | 4 | 7 | >48, >48 |
| *Sphyrana barracuda* VI-73 | 8 | 6 | 1.10, 4.66 |
| *Sphyrana barracuda* VI-65 | 5 | 4 | 16.0, <48 |
| *Sphyrana barracuda* VI-53 | 2 | 2 | 2.50, 6.40 |
| *Sphyrana barracuda* VI-85 | <1 | 2 | 1.21, 1.61 |
| *Sphyrana barracuda* VI-77 | 3 | 2 | 0.66, 0.63 |
| *Sphyrana barracuda* VI-38 | 1.5 | 2 | 0.33, 0.63 |

TABLE 1-continued

| SAMPLE | $ID_{50}$[a] 7 HR | $ID_{90}$[a] 22 HR | MOUSE ASSAY[b] SURVIVAL (HRS) |
|---|---|---|---|
| *Sphyrana barracuda* VI-57 | 4 | 2 | 0.50, 0.45 |
| PbTx-1 | 0.9 ng +/− 0.2 | 0.8 ng +/− 0.1 | — |

[a]mg muscle tissue equivalents (MTE)/well
[b]90 g MTE/kg mouse weight
[c]45 g MTE/kg mouse weight A significant advantage of the inventive cell bioassay is the rapidity of the method for the detection of sodium channel-activating toxins, such as brevetoxins and ciguatoxins, in comparison to the mouse bioassay. Mouse bioassays for brevetoxins and ciguatoxins involve long observation periods, ranging from several hours to 48 hours. See Hungerford et al., supra. The bioassay according to the invention typically can be effected within 4 to 6 hours of exposure to these toxins, with subsequent processing and development time taking only about 30 minutes.

The instant competitive assay for sodium channel-blocking toxins offers similar time advantages by allowing the detection of sodium channel-blocking toxins in only 4–22 hours, as opposed to the 24–48 hours previously required.

While the non-competitive assay of the present invention typically requires on the order of 24–48 hours for the determination of sodium channel-blocking toxins such as saxitoxin, such times are also typical of known cell-based assays. When the rapidity of the mouse bioassay is not required, such as in the analysis of embargoed shellfish or in research applications where small aliquots of isolates must be tested, the instant invention offers clear advantages as described above.

For convenience, kits can be provided for carrying out the inventive bioassay method. The kits may include the solutions utilized in the method of the invention, with all constituents in appropriate containers (vials, syringes, etc.) in predetermined proportions and amounts. The kits also may include means for contacting the solutions with the fluid sample, such as multi-well plates or test tubes. Where applicable, the kits may include an appropriate solvent for formazan, such as DMSO, and at least one calibration curve for a toxin having sodium channel-affecting activity.

Cell cultures employed in the bioassay can also be provided with the kits according to one embodiment of the invention. In some instances it may be necessary to provide the cells and the remaining components of the kits separately, maintained at different temperatures. In another embodiment, the multiwell plates or test tubes can be "pre-seeded" with the cell culture in a manner known to those skilled in the art, then shipped for overnight delivery to the user with the other kit components.

The inventive bioassay also is well-suited to automation, making possible the screening of large numbers of samples with minimal operator intervention. This provides for a convenient biological assay that can be accomplished within one day.

The MTT colorimetric test of cellular metabolism may be incorporated into the assay, resulting in an assay that is simpler than known methods. The MTT test is a rapid, versatile, quantitative, and simple technique to assess cell proliferation and cytotoxicity based upon the metabolism of MTT by mitochondrial dehydrogenase activity in viable cells. See Mossman, *J. Immuno. Meth.* 65: 55–63 (1983), the contents of which are hereby incorporated by reference. MTT is metabolized only in living cells, whose mitochondria cleave its tetrazolium ring to produce a blue colored product (formazan). The presence of formazan can be detected visually or spectrophotometrically and directly related to the number of living cells. The presence of toxins in the fluid sample is determined from the effect of the fluid sample on cell viability, as evidenced by the level of cell metabolism of MTT and resultant formazan production. Increased formazan production upon incubation with increasing concentrations of toxin from the fluid sample indicates cell rescue, and the presence of sodium channel-blocking toxins. Conversely, decreased formazan production indicates the presence of sodium channel-activating toxins.

In adapting the MTT test to the present invention, the cultured cells need only be contacted with the various fluids, the last being a solvent for formazan, such as DMSO, which facilitates the spectrophotometric measurement of the amount of formazan produced by the cell culture.

The present invention is described further by reference to the following, non-limiting examples.

EXAMPLE 1

Neuro 2A Cell Cultures

The metabolism of MTT has been reported to be minimal in some cell cultures. See, e.g., Carmichael et al., *Cancer Res.* 47: 936–42 (1987); Alley et al., *loc. cit.* 48: 589–601 (1988)). As shown below, the Neuro-2a cell line has been determined to be capable of effectively metabolizing MTT for the purposes of the inventive bioassay method.

Mouse neuroblastoma cells Neuro-2a (ATCC, CCL 131) were grown and maintained in RPMI 1640 (Sigma) containing 10% fetal bovine serum (Gibco), glutamine (2 mM) (Sigma), and sodium pyruvate (1 mM) (Sigma). Streptomycin and penicillin (Sigma) were also added at 50 $\mu$g and 50 units per ml, respectively, to form a growth medium (hereinafter "complete growth medium"). Cultures were maintained in an incubator at 37° C. with a humidified 5% $CO_2$:95% air atmosphere.

The ability of Neuro-2a cells to metabolize this tetrazolium salt as an index of viable cell number is show in FIG. 1. Cells were plated at the density indicated on the x-axis and allowed to recover for 24 hours at 37° C. prior to incubation with MTT for 15 minutes. Following solubilization in an appropriate solvent (here, DMSO), the amount of blue formazan product was then measured at 570 nm. Values shown in FIG. 1 represent the mean of 6 replicates, with the error bars indicating ±SD (standard deviation). Absorbance was proportional to initial cell inoculum and exhibited excellent reproducibility between replicate wells.

EXAMPLE 2

SK-N-SH and SK-N-MC Cell Cultures

Human cell lines were selected based upon the criteria set forth in Catterall et al., supra, and were tested for the presence of voltage-gated sodium channels by measuring their response in the present cell bioassay using a toxin standard. Cell lines that were (neuroblastomas) and were not (melanoma and colon adenocarcinoma) expected to possess voltage-gated sodium channels were tested.

Figure 8A:
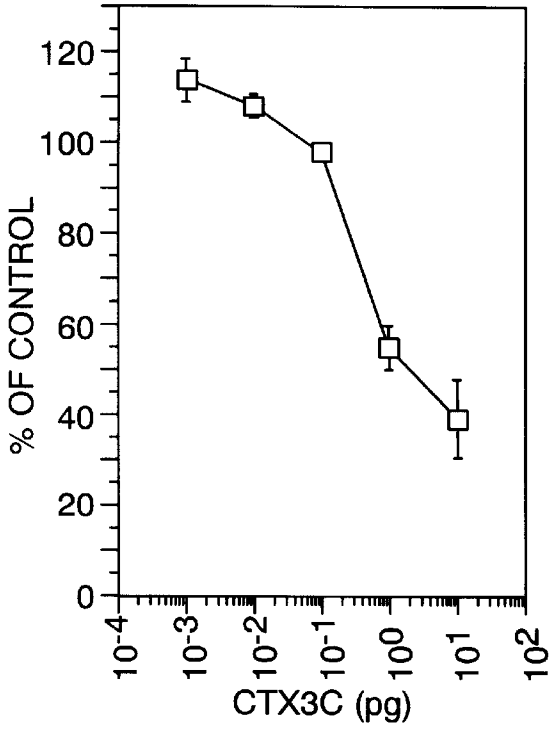
FIG. 8A shows human neuroblastoma SK-N-SH cells vs. ciguatoxin (CTX3C) in the presence of ouabain and veratridine.
Figure 8B:
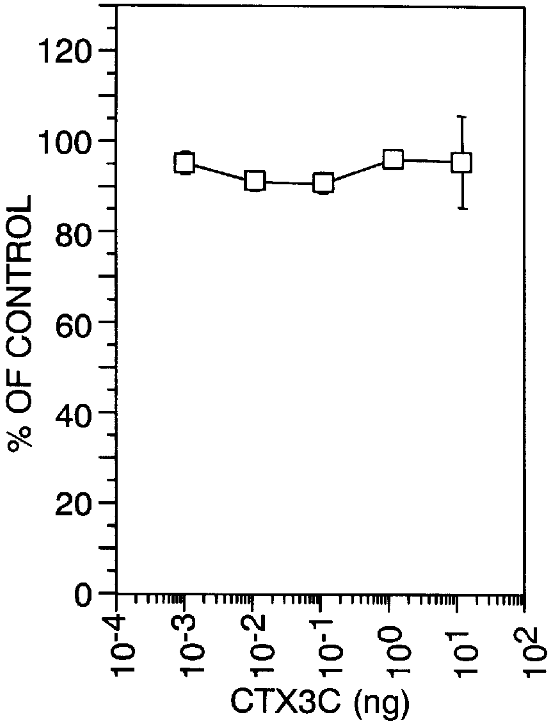
FIG. 8B shows human neuroblastoma SK-N-SH cells vs. ciguatoxin (CTX3C) alone (no ouabain or veratridine)
Figure 9A:
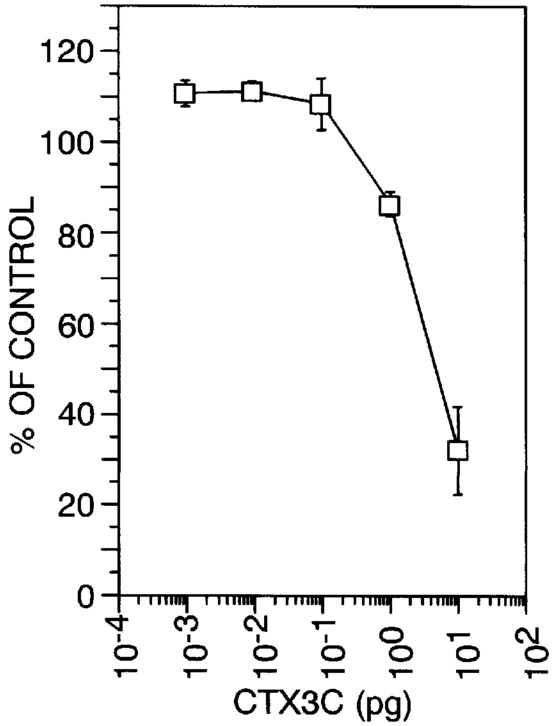
FIG. 9A shows human neuroblastoma SK-N-MC vs. cells ciguatoxin (CTX3C) in the presence of ouabain and veratridine.
Figure 9B:
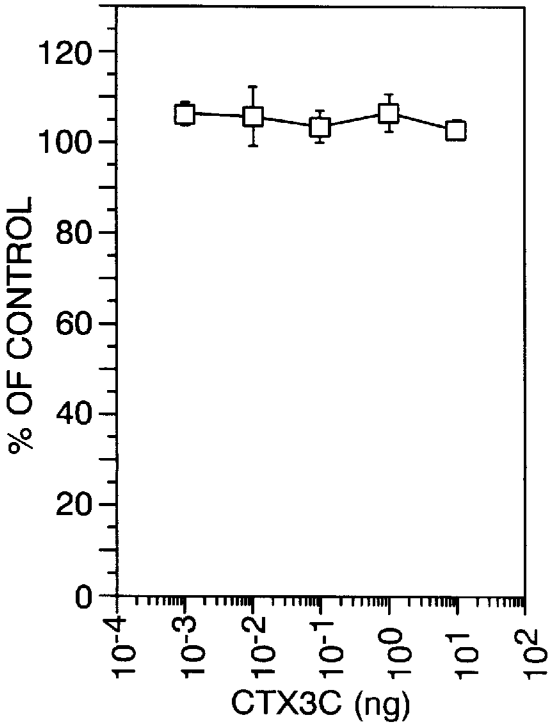
FIG. 9B shows human neuroblastoma SK-N-MC cells vs. ciguatoxin (CTX3C) alone (no ouabain or veratridine)
Figure 10A:
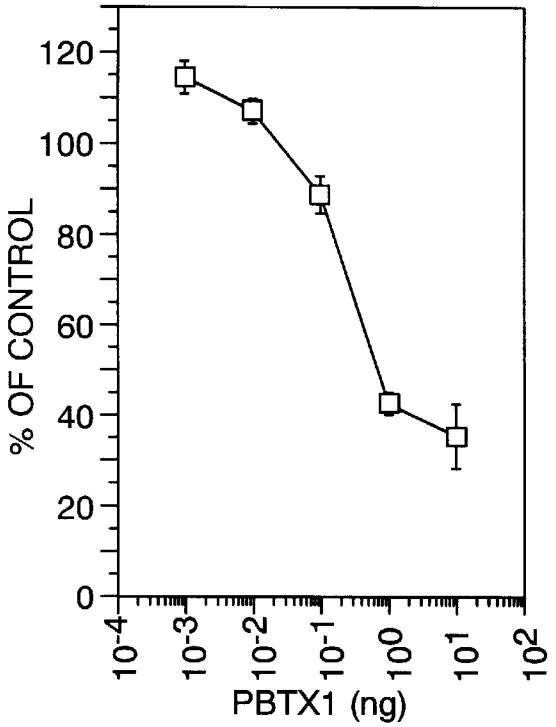
FIG. 10A shows human neuroblastoma SK-N-SH cells vs. brevetoxin (Pbtx-1) in the presence of ouabain and veratridine.
Figure 10B:
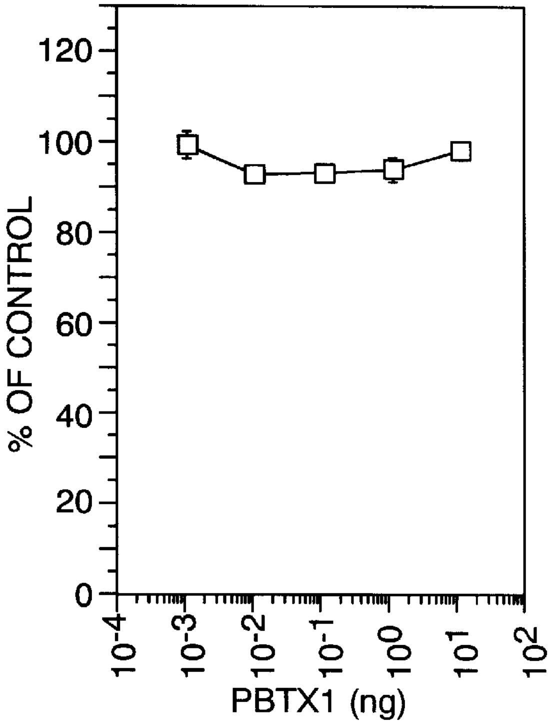
FIG. 10B shows human neuroblastoma SK-N-SH cells vs. brevetoxin (pbtx-1) alone (no ouabain or veratridine)

FIG. 8A shows that human neuroblastoma SK-N-SH exhibited a dose-dependant cytotoxicity in the presence of ciguatoxin (CTX3C) and ouabain and veratridine. FIG. 9A shows that human neuroblastoma SK-N-MC exhibited a dose-dependant cytotoxicity in the presence of ciguatoxin (CTX3C) and ouabain and veratridine. FIG. 10A shows that human neuroblastoma SK-N-SH exhibited a dose-dependant cytotoxicity in the presence of brevetoxin (PbTx-1) and ouabain and veratridine. FIGS. 8B, 9B and 10B show that the dose-dependent cytotoxicity also is dependent on the presence of ouabain and veratridine.

Figure 11A:
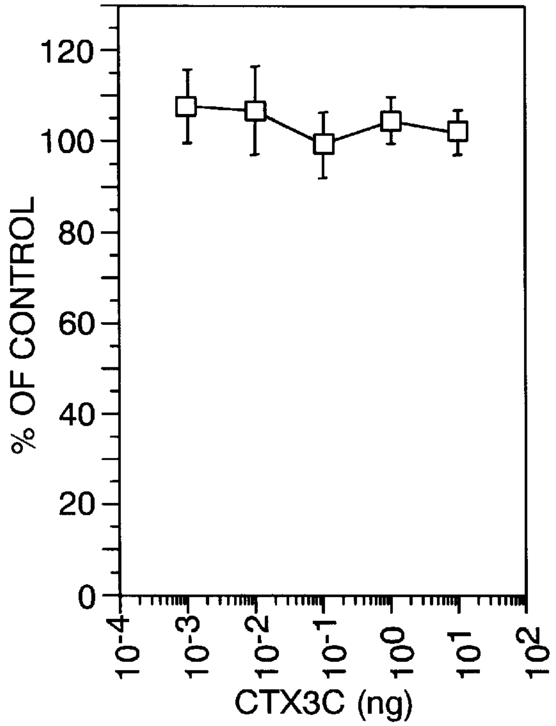
FIG. 11A shows human melanoma cells demonstrating a lack of response to ciguatoxin in the presence of ouabain and veratridine.
Figure 11B:
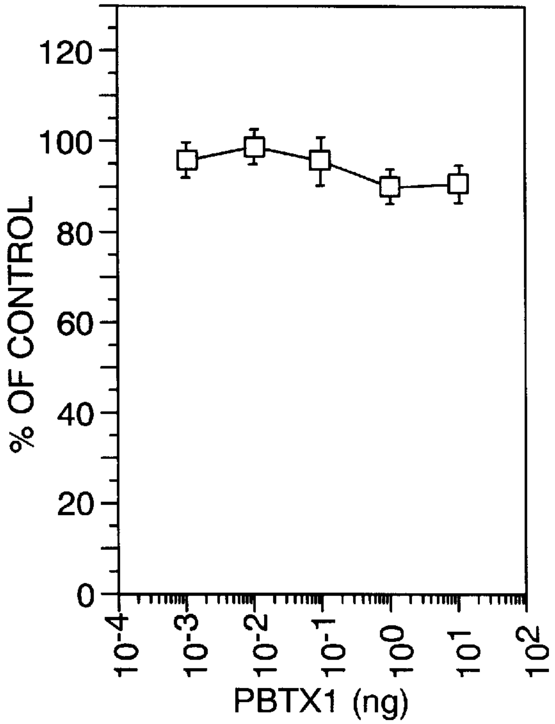
FIG. 11B shows human melanoma cells vs. brevetoxin, demonstrating a lack of response to brevetoxin in the presence of ouabain and veratridine.
Figure 12A:
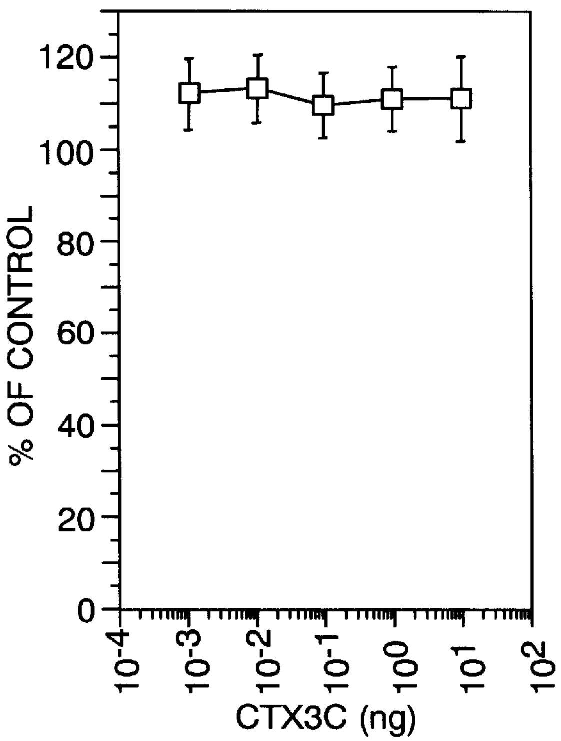
FIG. 12A shows human colon carcinoma HT-29 cells vs. ciguatoxin, demonstrating a lack of response to ciguatoxin in the presence of ouabain and veratridine.
Figure 12B:
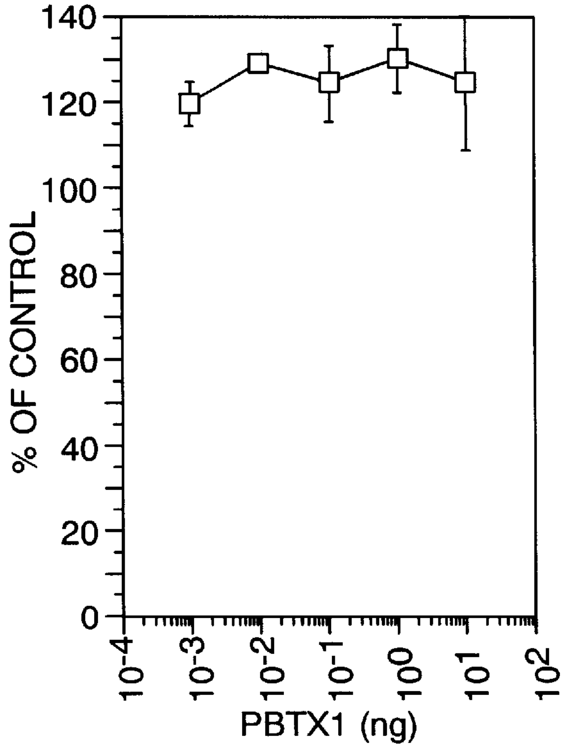
FIG. 12B shows human colon carcinoma HT-29 cells vs. brevetoxin, demonstrating a lack of response to brevetoxin in the presence of ouabain and veratridine.

FIGS. 11A and 11B show that a human melanoma does not respond to either ciguatoxin (FIG. 11A) or brevetoxin (FIG. 11B). FIGS. 12 and 12B show similar results for human colon carcinoma HT-29 (ATCC HTB-38).

EXAMPLE 3

Saxitoxin Cell Bioassay

Purified saxitoxin, obtained from Calbiochem, was diluted in phosphate-buffered saline (PBS), pH 7.4 and maintained as a frozen stock at −20° C. Prior to assay the saxitoxin stock was diluted to the appropriate concentration with complete growth medium.

Cultures were prepared for bioassay as described by Jellett et al., supra, with the modifications described below. Cells were harvested with a trypsin EDTA solution (0.5%/0.2%) (Sigma) in PBS and seeded into 96-well plates (CoStar) at a density of $5\times10^5$ cells/ml in 200 μl complete growth medium per well. The cultures were incubated at 37° C. under a 5% $CO_2$ atmosphere for approximately 24 hours before proceeding further.

The culture wells received 10 μl of sample and 10 μl additions of aqueous stocks of 10 mM ouabain (Sigma) and 1 mM veratridine (Sigma), pH 2. Each sample concentration was tested in replicate (3 to 5 wells). A minimum of 15 wells per plate were processed as ouabain/veratridine-treated controls (no sample addition, 0.5 mM ouabain, 0.05 mM veratridine), and a minimum of 5 wells served as untreated controls (without ouabain/veratridine and without sample). Control wells received added culture medium to make up for volume differences of sample and ouabain/veratridine (up to 30 μl per well). The cultures were then incubated for 24–48 hours.

MTT (3-(4,5-dimethylthiazol-2-yl)-2,5-diphenyltetrazolium bromide (Sigma)), was prepared as a 5 mg/ml stock solution in PBS, pH 7.4, and stored at 4° C. until use. Following incubation with the samples, the overlaying medium was removed from each of the cultures, and, without a wash step, 60 μl of a 1:6 dilution of the MTT stock in complete growth medium was added to each well. The cultures were then incubated for approximately 15 minutes at 37° C., or until a suitable deposit of reduced dark formazan deposit was observed in control wells (occasionally up to 30–45 minutes). The incubation medium was then removed, and without an intermediate rinsing step, 100 μl of DMSO was added to each well. The plates were immediately read on a Dynatech MR-5000 automated multiwell scanning spectrophotometer using a test wavelength of 570 nm and a reference wavelength of 630 nm.

Morphological alteration and subsequent cell loss was observed in cells incubated with 0.5 mM ouabain and 0.05 mM veratridine. This effect was maximal between 24–48 h, in agreement with previous reports. See Kogure et al. and Jellett et al., supra. Saxitoxin-dependent cell rescue was measured directly by alterations in MTT metabolism, as shown in FIG. 2 (values represent the mean of 3–4 replicates).

Figure 2A:
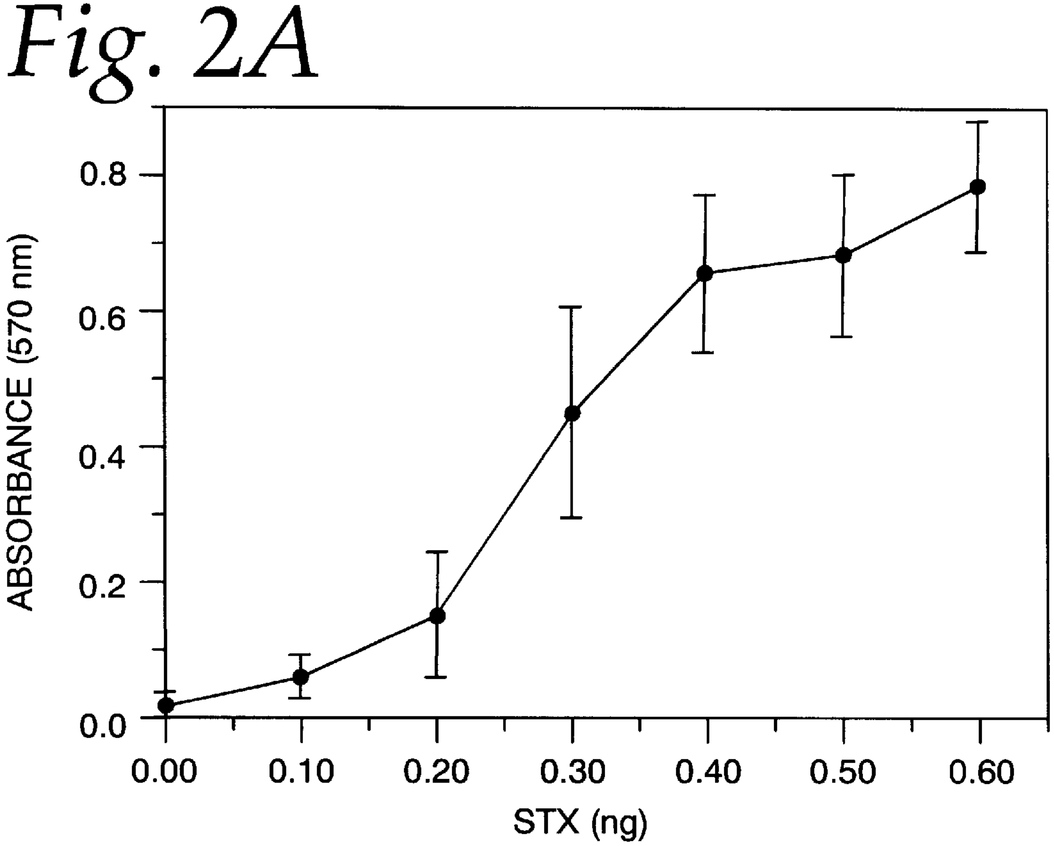
FIGS. 2A and 2B are graphs of the effect of increasing concentration of pure saxitoxin upon MTT development in a bioassay of the present invention.
Figure 2B:
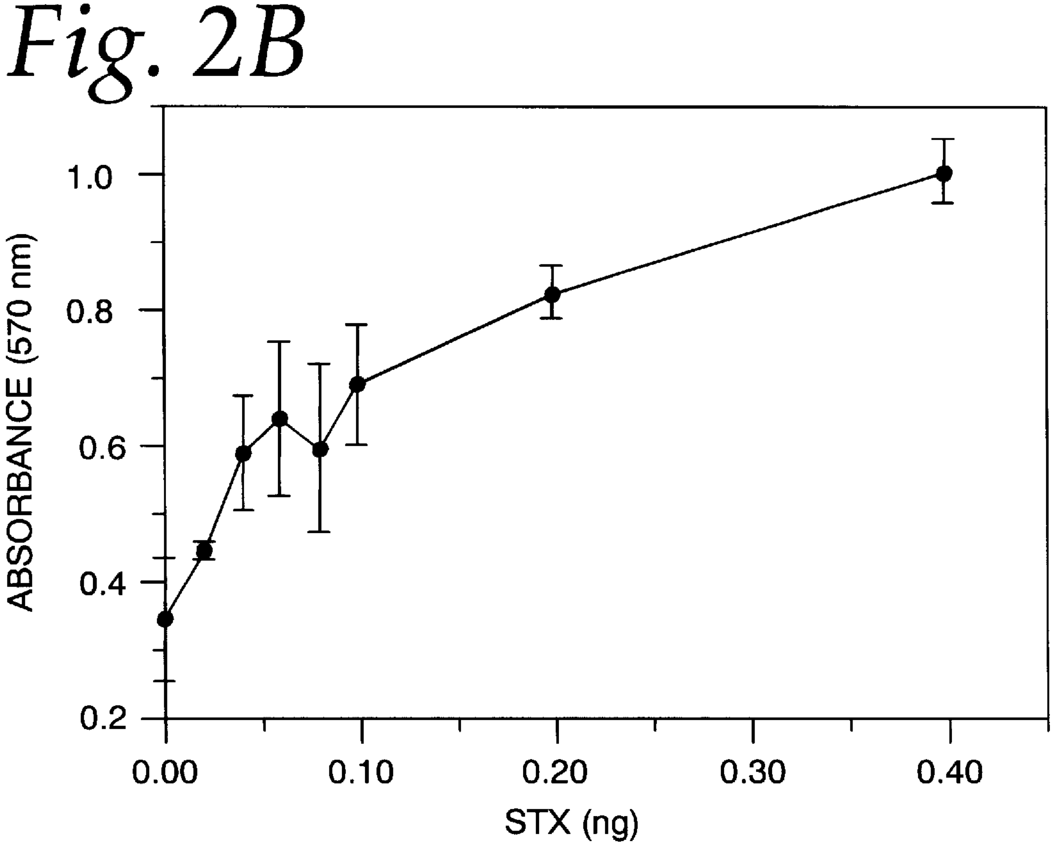

Purified saxitoxin was detected at a level of 0.1 ng/10 μl addition using an approximate MTT development time of 15 minutes (see FIG. 2*a*). Assay sensitivity could occasionally be enhanced by increasing MTT development time to approximately 45 minutes, with a resultant detection limit of about 0.02 ng/10 μl addition (see FIG. 2*b*). However, with added MTT development time the assay tended to plateau at higher concentrations of saxitoxin. Assay sensitivities were comparable to that reported by Jellett et al., supra. In the absence of ouabain/veratridine treatment, saxitoxin at the concentrations tested had no measurable effect. (For the purpose of comparison, 0.1 ng/10 μl and 0.02 ng/10 μl saxitoxin are equivalent to shellfish extracts of 2 μg/100 g tissue and 0.4 μg/100 g tissue, respectively.)

EXAMPLE 4

Cell Bioassay of Crab Viscera

To test the applicability of the inventive bioassay for the detection of naturally incurred PSP in samples, acid extracts of viscera from Dungeness crab, *Cancer magister*, were examined. The crab viscera extracts were generously made available by Cheryl Eklund and James Bryant, FDA, Bothell, Washington. Toxicity levels were determined previously by mouse bioassay of the entire visceral portions of the crabs. See OFFICIAL METHODS OF ANALYSIS OF THE AOAC, par. 959.08, 881 (K. Helrich, ed. 1990).

Two extracts exhibiting positive and negative PSP activity by the AOAC mouse bioassay (122 μg/100 g and none detected/100 g respectively) were tested at various dilutions in the cell bioassay. Cultures were prepared for bioassay, incubated and assayed as described in Example 3.

Figure 3:
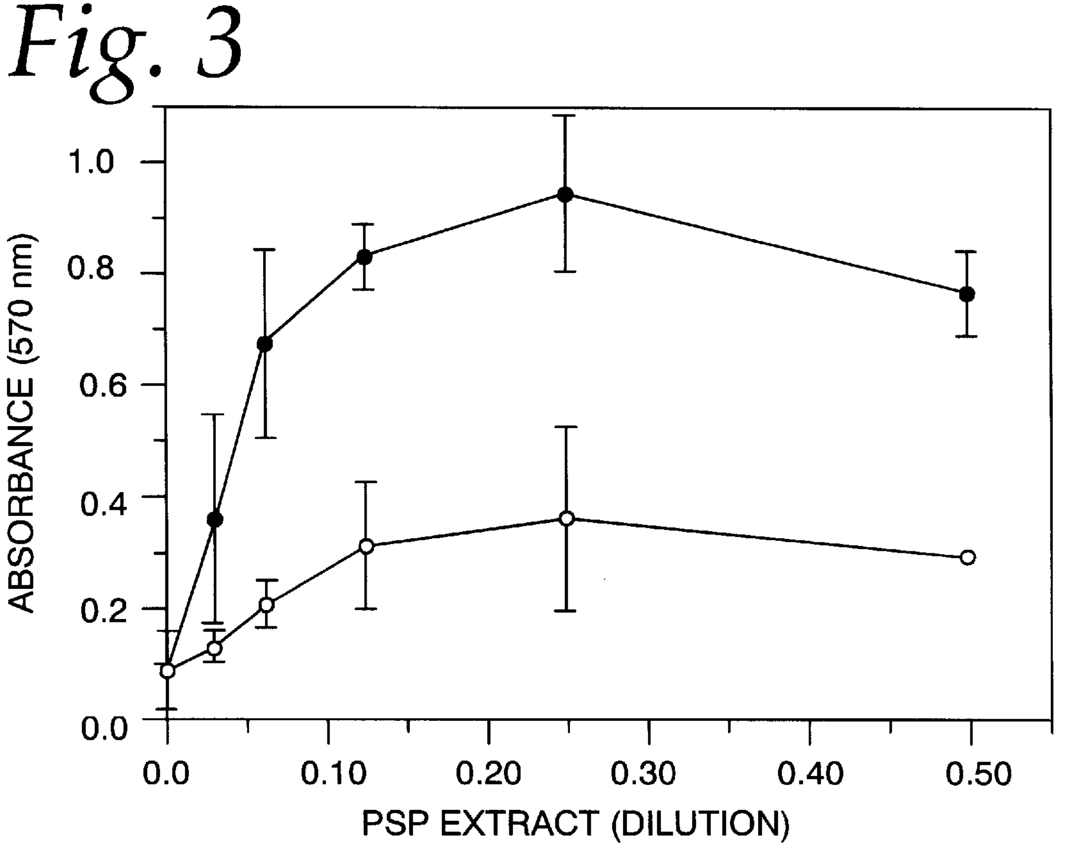
FIG. 3 is a graph of PSP toxin activity in aqueous Dungeness crab extracts as determined by an inventive bioassay.

Levels of saxitoxin activity were calculated by comparing linear portions of the crab viscera dose response curves (dilutions of 1/32, 1/16, and 1/8) with a standard curve derived using pure saxitoxin, and multiplying interpolated toxin concentrations by the appropriate dilution factor. Results are set forth in FIG. 3, in which (●) and (○) indicate extracts testing at 122 μg/100 g and no detectable activity using the standard mouse bioassay, respectively.

As calculated from the three highest dilutions, the cell bioassay detected mean values (with standard deviations) of 124±44 μg/100 g in the positive extract (mouse bioassay). Interestingly, the extract that was PSP-negative by mouse bioassay had a mean value of 33±2 μg/100 g tissue in the inventive bioassay. This level of saxitoxin is below the standard detection limit of the animal test (40 μg/100 g).

The dose response curves tended to plateau with increasing concentrations of extract (dilutions of less than 1:4), suggesting a competing or potentially interfering cytotoxic component.

EXAMPLE 5

Brevetoxin Cell Bioassay

Brevetoxins PbTx-1 and PbTx-3 (Calbiochem) were dissolved in methanol to form a stock. Prior to assay brevetoxin stock solution was diluted 1:100 in complete growth medium, from which serial dilutions in complete growth medium were then made. The cultures were prepared for bioassay as described in Example 3, except that 10 μl samples were added to replicate culture wells in both the presence and absence of ouabain and veratridine. The cultures were then incubated for 2–22 hours.

Figure 4A:
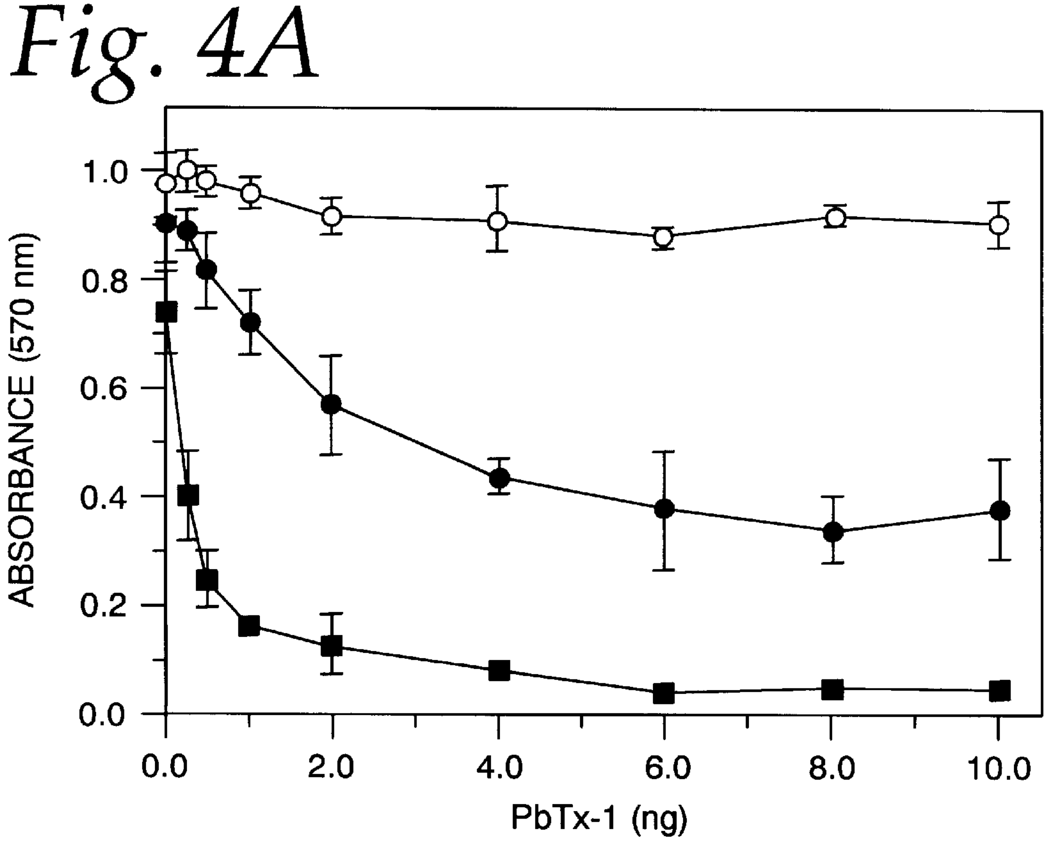
FIGS. 4A and 4B are graphs of brevetoxin PbTx-1 cytotoxicity as measured by an inventive assay.
Figure 4B:
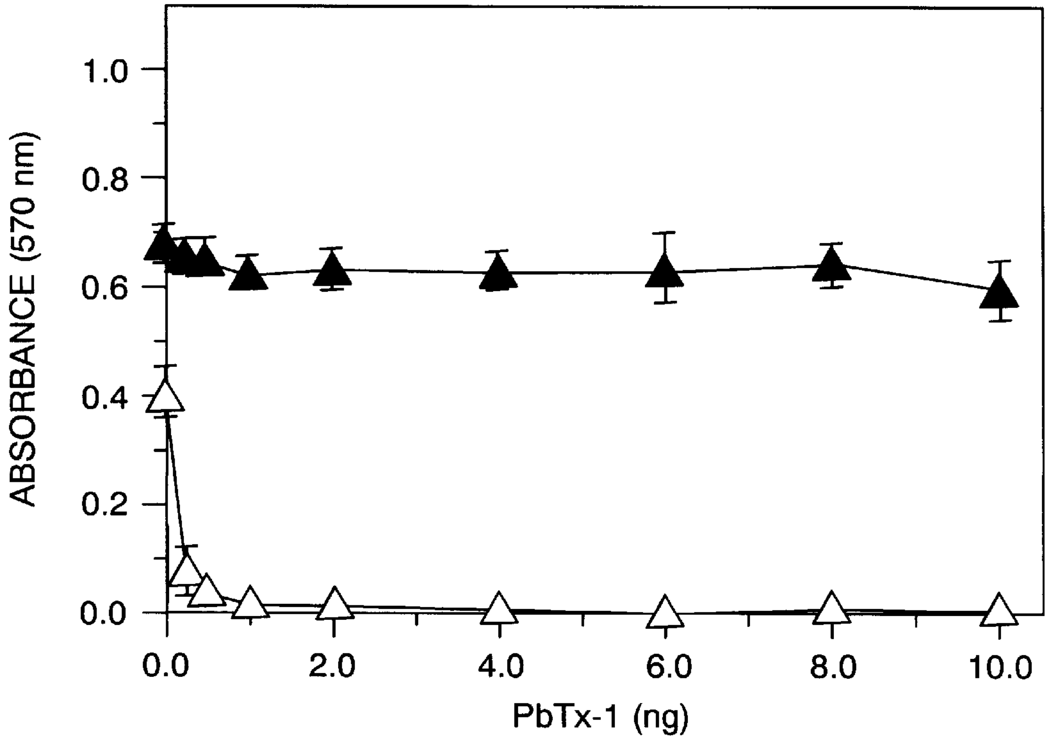

The cell bioassay was performed essentially as described in Example 3 for saxitoxin. However, instead of measuring cell rescue, an assessment of toxin-enhanced cytotoxicity in the presence of ouabain/veratridine was performed. The effect of increasing concentrations and time of exposure of brevetoxin PbTx-1 in the cell bioassay are shown in FIGS. 4A and 4B. In the figures, brevetoxin cytotoxicity was assayed at 2 hours (○), 4 hours (●), 6 hours (■) and 18 hours (Δ). Values represent the mean of four replicates.

In the dose range explored, titratable cytotoxicity was observed as early as 4 hours (FIG. 4A) and was essentially total at 18 hours. Brevetoxin in the absence of ouabain/veratridine was not cytotoxic even at the highest concentration and incubation time tested (10 ng/10 μl, 18 hours exposure(A)) (FIG. 4B). PbTx-3 produced similar results as observed for PbTx-1 in the cell bioassay.

EXAMPLE 6

Ciguatoxin Cell Bioassay

A ciguatoxic fish extract (methanol fraction), prepared from wrasse, *Cheilinus rhodochrous*, was generously provided by Dr. Yoshitsugi Hokama, University of Hawaii. A stock solution of this material was prepared in the same manner as the brevetoxins in Example 5.

Figure 5:
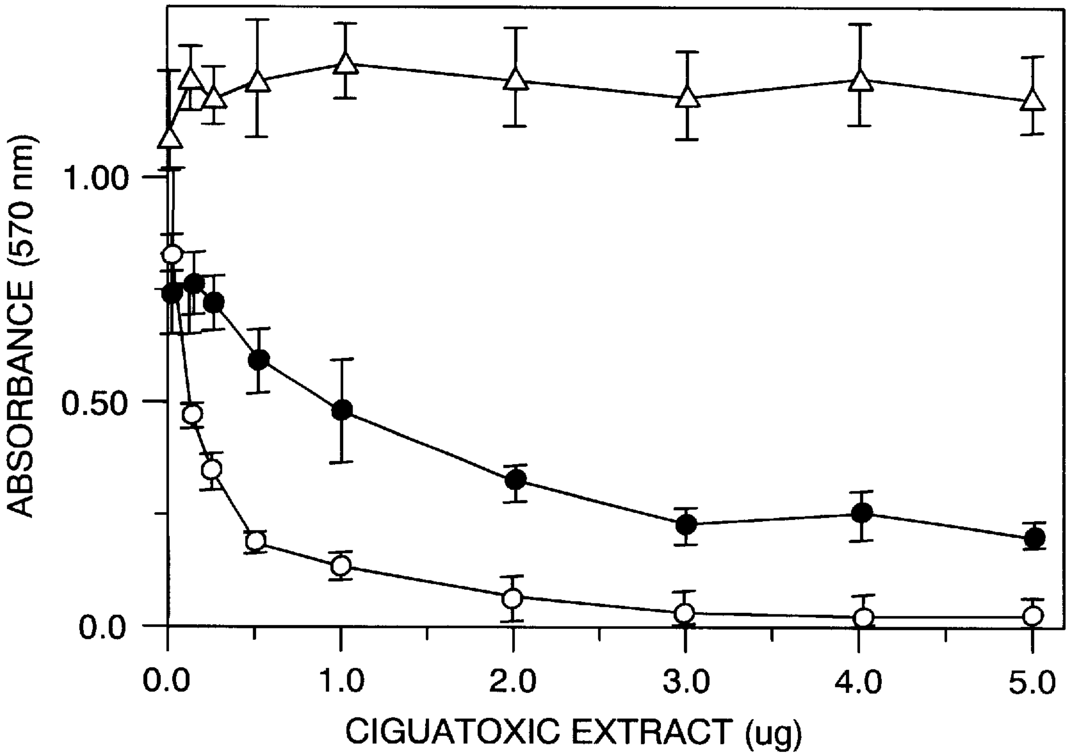
FIG. 5 is a graph of ciguatoxin activity in wrasse extracts, as determined by an assay within the present invention.
Figure 6A:
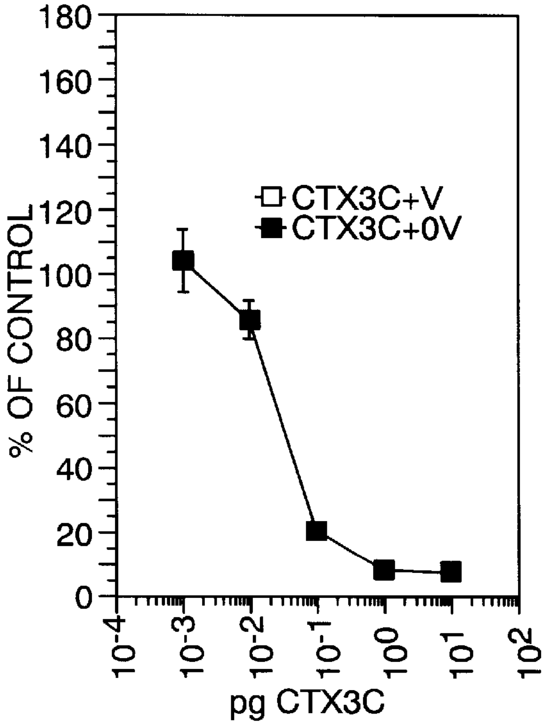
FIG. 6A shows Neuro 2a cells vs. CTX3 (22 hr exposure) in the presence of ouabain and veratridine.
Figure 6B:
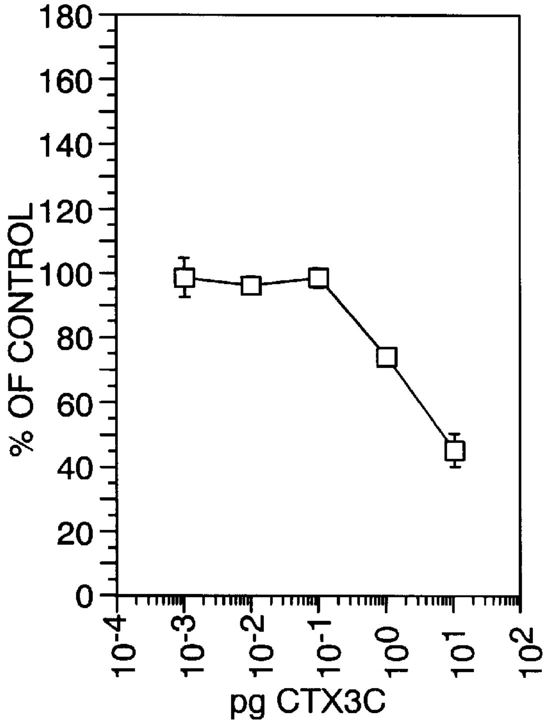
FIG. 6B shows Neuro 2a cells vs. CTX3 (22 hr exposure) in the presence of veratridine alone.

Cultures were prepared for bioassay, incubated and assayed as described in Example 5. The extract was diluted and applied to the cells in the presence or absence of ouabain/veratridine. Within 6 hours the sample produced significant dose-dependent cytotoxicity only in cells treated with ouabain/veratridine (data obtained at 6 hours (●) and 22 hours (○)), as shown in FIG. 5 (values represent the mean of four replicates). Even after prolonged exposures of up to 22 hours the ciguatoxic extract was not cytotoxic in the inventive cell bioassay in the absence of ouabain/veratridine treatment (data obtained at 22 hours (Δ)).

EXAMPLE 7

Quantitative Cell Bioassay for Ciguatoxin

Serial dilutions are made with three samples (labeled X, Y and Z) and one toxin standard. Each dilution is incubated with Neuro 2a cells in the presence of veratridine and ouabain for 4 to 24 hours. Each dilution is then incubated with XTT and the formation of formazan is read colorimetrically. X and Y produce a ouabain/veratridine-dependent reduction in formazan reaction product consistent with the presence of ciguatoxins, whereas Z is inactive (qualitative determination).

A 1/50 dilution of sample X and a 1/1000 dilution of sample Y produce a 50% response in the cell assay. From the toxin standard curve generated with purified ciguatoxin (i.e. CTX-1), it is observed that a 1 pg dose of pure toxin also results in a 50% cell assay response. Thus, samples X and Y at the dilution indicated have the equivalent of 1 pg of ciguatoxin. The amount of toxin equivalents present in the original undiluted samples is calculated by multiplying by the dose by the appropriate dilution factor (50 and 1000), resulting in 50 pg and 1000 pg CTX-1 equivalents for samples X and Y, respectively.

EXAMPLE 8

Cell Bioassay Using Crude Extracts

Acetone-Chloroform Extracts

Figure 13:
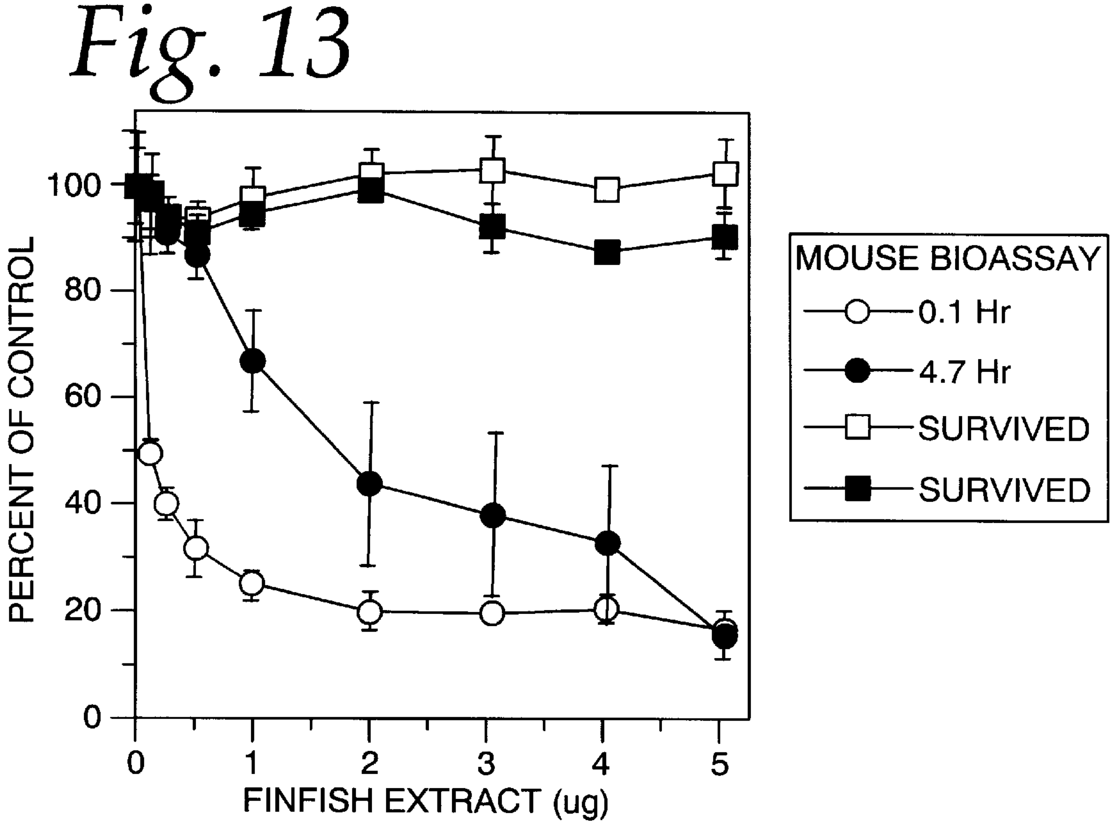
FIG. 13 shows the results of a cell bioassay of pacific region finfish extracts with comparative mouse toxicity data (100 mg dose). Extract concentration is in μg addition per well. Values represent the mean of 4 replicates. The error bars indicate ±CV. ○ indicates a mouse death time of 0.1 hr; ● indicates a mouse death time of 4.7 hr; ■ and □ indicate non-lethal in mice.

Crude extracts of Pacific finfish prepared by the acetone-chloroform method of Kimura et al., supra, were well tolerated, without apparent matrix problems by the cell bioassay, and produced results in accordance to in vivo toxicity (FIG. 13). The most potent of these extracts (○), $ID_{50}$ of 0.13 μg cell bioassay and mouse death time of 0.1 hr (50 mg dose), was obtained from the flesh of a barracuda implicated in human ciguatera intoxication. An extract of intermediate toxicity by mouse bioassay (4.7 hr survival) exhibited comparative mid-range activity by cell bioassay (●), and two samples that were non-lethal in mice were devoid of activity in the cell bioassay (□,■).

Abbreviated Extract

Success with the acetone-chloroform extracts encouraged efforts to even further simplify sample preparation. For the first study, flesh from a single ciguatoxic barracuda (confirmed human intoxication) was pooled and homogenized. The abbreviated extraction procedure was essentially nothing more than the initial steps of conventional sample preparation, consisting of blending with acetone, filtration, and a single concentration step before dilution with methanol. This simple procedure was completed within 3 hr.

A conventional semi-purified extract was prepared from the finfish homogenate using organic and aqueous wash steps and silica column chromatography. This sample was prepared by Dr. Robert Dickey, U.S. FDA, Dauphin, Ga. The standard extraction required approximately 2 days of processing.

Figure 14:
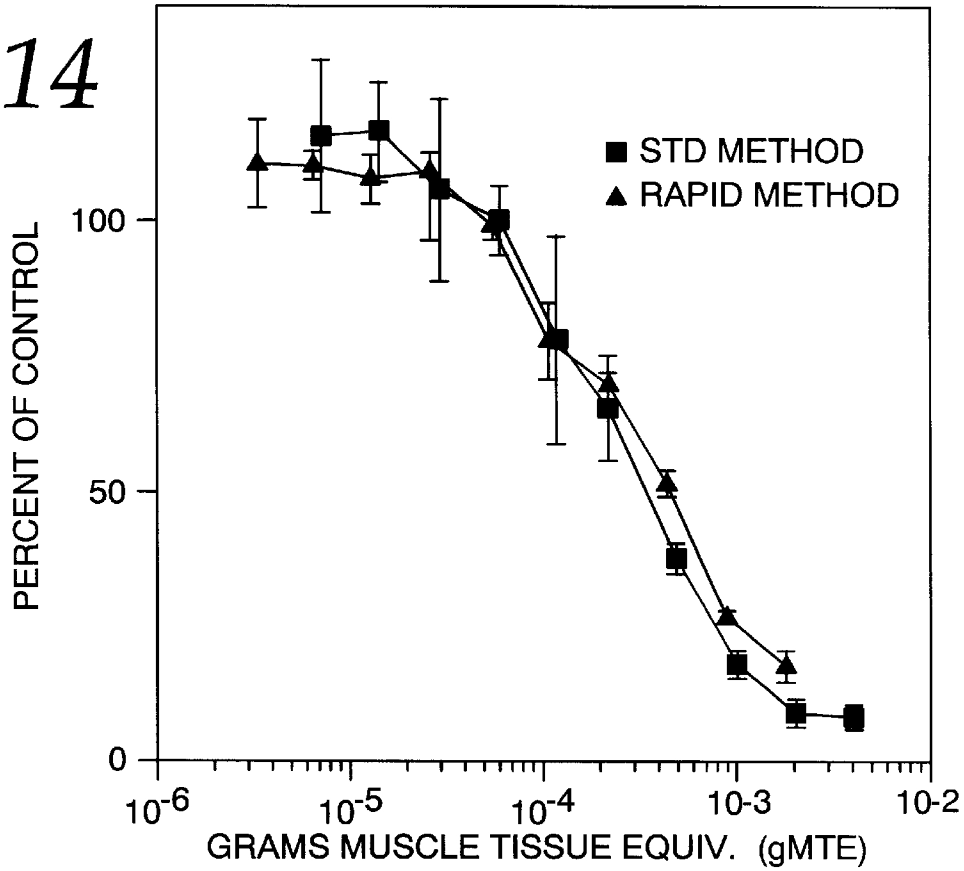
FIG. 14 shows the results of a comparative cell bioassay analysis of semi-purified (■) and crude (▲) extracts prepared from the same ciguatoxic fish. Values represent the mean of 4 replicates. The error bars indicate ±CV.

FIG. 14 shows that both extracts (■-standard method, ▲-rapid method) exhibited nearly identical activity by cell bioassay, with $ID_{50}$ values of approximately 0.4 μg of muscle tissue equivalents. The results obtained using this simple and rapid initial extraction testify to the high tolerance of impurities by the cell bioassay. In addition, the cell bioassay was approximately 5 orders of magnitude more sensitive at the 50% response dose than the mouse bioassay (the semi-purified extract produced an $LD_{50}$ of approximately 12.1 gMTE/20 g mouse, in agreement with the enhanced sensitivity observed with purified ciguatoxins).

An even more simplified procedure also has been used successfully. In this simple extraction procedure, the flesh of an animal is blended with a suitable solvent, such as acetone or methanol, the resulting mixture is filtered, and the assay is performed on the solution.

EXAMPLE 9

Simplified Bioassay for Sodium Channel-Activating Toxin

The general protocol is as follows: Neuro-2a cells are placed as 1 ml suspensions of $1.5\times10^6$ cells into 5 ml polystyrene snap cap tubes. Appropriate tubes then receive 150 μl ouabain stock (10 mM), 150 μl veratridine stock (1 mM), and different concentrations of sample and standard. Tubes then receive 2 ml of 45° C. suspension agar (1% Bacto-agar, 0.4% glucose, 0.003% methylene blue, in PBS pH 7.2), are mixed by inversion, and placed in an ice slurry till solidified (approximately 2–5 min). Tubes then are incubated at 37° C. for 4–24 hr, and decolorization of methylene blue is noted an indicator of cell viability.

Simplified Bioassay for Ciguatoxin CTX3C

Agar gel was melted and maintained at 45° C. Medium from the tissue culture flask was decanted and replaced with EDTA lifting solution. The cells were incubated in this solution for about 5 minutes until they were suspended. 4 mL Test tubes were prepared with 1 mL of a suspension of Neuro 2A cells at three different concentrations, with and without approximately 100 μl CTX3C and with 2 mL agar mix with and without ouabain and veratridine, for a total of 12 tubes. An additional test tube with no cells (but with CTX3C and agar with ouabain and veratridine) also was prepared. Methylene blue was added to each test tube, and the tubes were chilled on ice for about five minutes until the agar suspension solidified. The tubes were incubated at 37° C. for about 4 hours.

Figure 15:
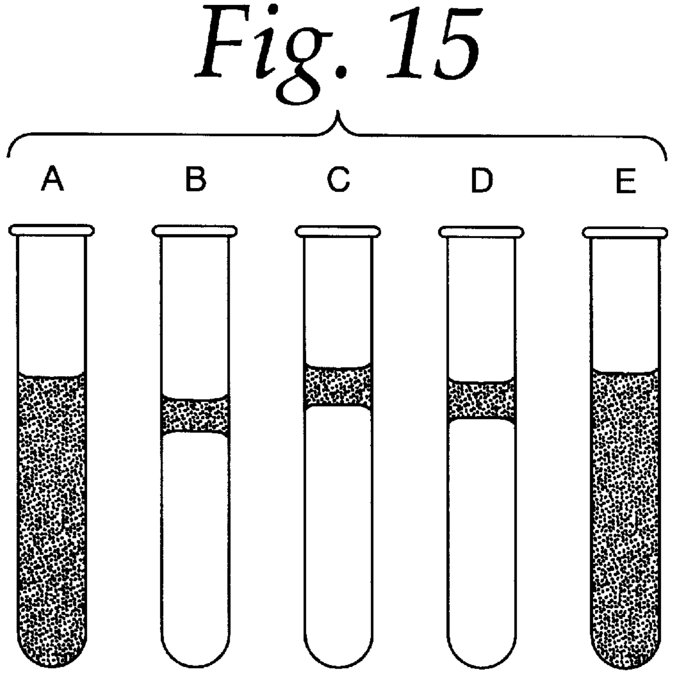
FIG. 15 shows the results of a suspension-cell tube assay detection of CTX3C. All tubes contain methylene blue in an agar base with the following additions: Tube A: CTX3C, ouabain/veratridine, and cells; Tube B: CTX3C and cells; Tube C: ouabain/veratridine and cells; Tube D: cells; Tube E: no additions.

FIG. 15 shows detection of 0.15 ng CTX3C at 4 hour in another example of the suspension-cell tube assay. In the presence of ouabain and veratridine, CTX3C inhibited decolorization of methylene blue (tube A). Detection was specific for a sodium channel activating toxin as evidenced by the lack of effect upon methylene blue decolorization for CTX3C in the absence of ouabain/veratridine (tube B). Development was complete in 4 hours and stable for up to 24 hours. Similar results were obtained by layering aqueous solutions of CTX3C onto the surface of precast cell suspensions; however, methylene blue decolorization was not as distinct, possibly due to diffusion effects (data not shown).

EXAMPLE 10

Competitive Bioassay for Saxitoxin

An analysis of brevetoxin PbTx-1 antagonism with saxitoxin was done by titrating each agent against the other, using standard cell assay conditions in 96 well plates, to generate isobolographs as per the method of Roos et al., *P.N.A.S., USA* 84: 4860–4864 (1987) (data not shown). From these experiments a fixed concentration of 6 ng PbTx-1 was chosen as a suitable concentration for antagonism analysis.

Figure 16:
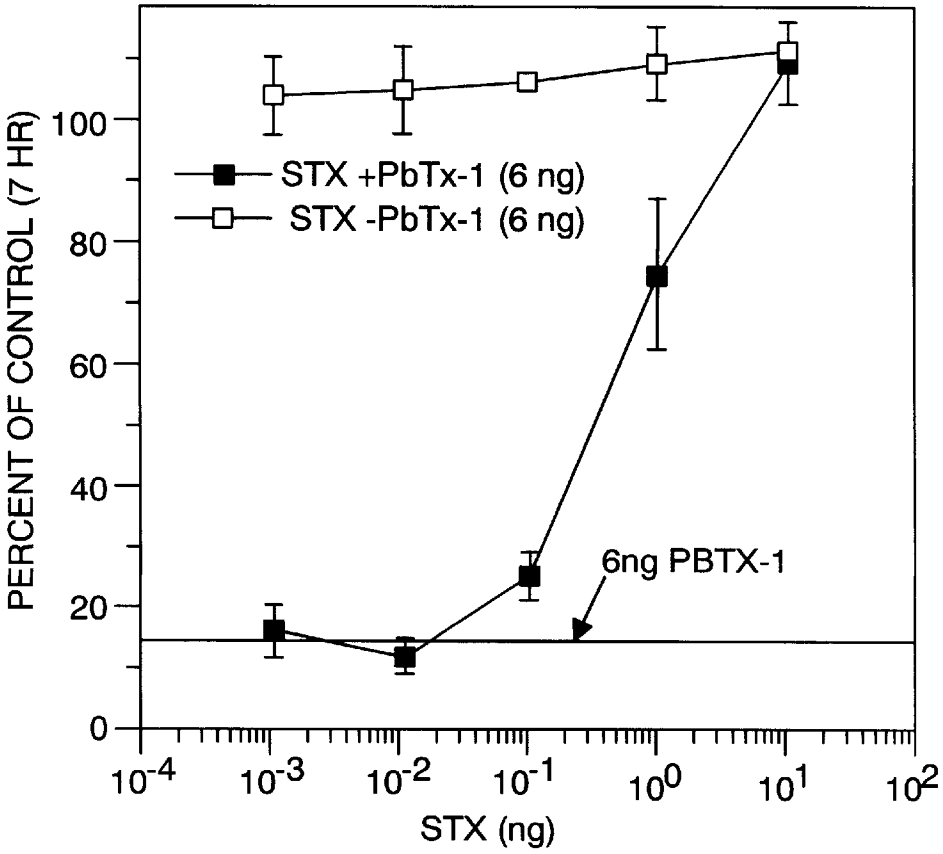
FIG. 16 shows the results of a cell bioassay detection of saxitoxin by PbTx-1 antagonism. Toxin concentration is in ng addition per well. Values represent the mean of 4 replicates. The error bars indicate ±CV. ■ saxitoxin with PbTx-1; □ saxitoxin without PbTx-1.

FIG. 16 shows the detection of saxitoxin at 7 hr in the presence of a fixed concentration of PbTx-1 (6 ng) (■). The lower level of detection was 0.1 ng saxitoxin and response was linear up 10 ng (the highest dose evaluated). These results are comparable to the dose range observed in the standard cell bioassay requiring from 24–48 hr. The dose-dependent antagonism of PbTx-1 with saxitoxin is in agreement with assessing activity based upon interactions at the level of voltage-gated sodium channels.

EXAMPLE 11

Kit for Bioassay

The following components are combined in packaged form (liquid solutions in appropriate containers):

| | |
|---|---|
| ouabain/veratridine solution (0.5 mM/0.05 mM) | 5–25 ml |
| MTT solution (5 mg/ml in PBS, pH 7.4) | 5–25 ml |
| toxin standard | 5–25 ml |
| Neuro 2A cells (adherent cultures in T flasks) | 1–5 × $10^7$ cells |
| EDTA lifting solution | 25 ml |
| 96-well plate | |

EXAMPLE 12

Kit for Simplified Bioassay

The following components are combined in packaged form (liquid solutions in appropriate containers):

| | |
|---|---|
| Neuro 2A cells (adherent cultures in T flasks) | 1–5 × $10^7$ cells |
| EDTA lifting solution | 25 ml |

-continued

| | |
|---|---|
| Agar gel premixed with methylene blue and ouabain and veratridine | 10–50 ml |
| toxin standard | 5–25 ml |

It will be apparent to those skilled in the art that various modifications and variations can be made to the processes and compositions of this invention. Thus, it is intended that the present invention cover the modifications and variations of this invention provided they come within the scope of the appended claims and their equivalents.

What is claimed is:

1. A cell bioassay method for determining the presence in a fluid sample of a toxin having sodium channel-blocking activity, which method comprises the steps of:

(a) incubating, in the presence of a portion of said fluid sample, a culture of cells which express voltage-gated sodium channels and which are responsive in a dose-dependent manner to sodium channel-activating toxins with a medium comprising (i) an agent which causes persistent activation of the voltage-gated sodium channel and (ii) a sodium channel-activating toxin;

(b) incubating said culture with a medium comprising an indicator which is acted upon by living cells to generate a discernable result, and (c) observing said culture for an incidence of said result, whereby an observation of reduction of sodium channel-activating toxin induced cytotoxicity is correlated with the presence of said sodium channel-blocking toxin in said sample.

2. A cell bioassay according to claim 1, wherein said incubation is carried out for about 2 to 22 hours.

3. A cell bioassay according to claim 2, wherein said incubation is carried out for about 4 to 6 hours.

4. A cell bioassay according to claim 1, wherein said agent of step (a) is selected from the group consisting of veratridine, aconitine, batrachotoxin, and grayanotoxin.

5. A cell bioassay according to claim 4, wherein said agent additionally comprises ouabain.

6. A cell bioassay according to claim 1, wherein said sodium channel-blocking toxin is selected from the group consisting of saxitoxin, neosaxitoxin, gonyautoxin, and tetrodotoxin.

7. A cell bioassay according to claim 1, wherein said sodium channel-activating toxin is selected from the group consisting of ciguatoxins and brevetoxins.

8. A cell bioassay according to claim 1, wherein said indicator is selected from the group consisting of 3-(4,5-dimethylthiazol-2-yl)-2,5-diphenyl tetrazolium bromide (MTT), 2,3-bis (2-methoxy-4-nitro-5-sulfophenyl)-2H-tetrazolium-5-carboxanilide inner salt (XTT) and methylene blue.

9. A cell bioassay according to claim 1, wherein said toxin is detected at a level of 0.1 ng/10 μl.

10. A cell bioassay according to claim 1, wherein said steps (a) and (b) are effected together, such that said indictor is contained in said medium.

11. A cell bioassay according to claim 10, wherein said medium is a matrix which holds viable cells in a semi-solid suspension.

12. A cell bioassay according to claim 11, wherein said matrix is selected from the group consisting of agar, aragose, methyl cellulose, gelatin and coagulated plasma.

13. A cell bioassay according to claim 1, wherein the correlation of said result is effected by relating said result to a standard calibration curve.

14. A cell bioassay according to claim 1, wherein step (c) is effected by colorimetric means.

15. A cell bioassay according to claim 1, wherein:

step (a) comprises incubating, in the presence of a portion of said fluid sample, a plurality of said cultures of cells with said medium comprising (i) an agent which causes persistent activation of the voltage-gated sodium channel and (ii) a sodium-channel activating toxin, each of said cultures being incubated with a different concentration of said fluid sample, step (b) comprises incubating each of said cultures with said medium comprising an indicator which is acted upon by living cells to generate a discernable result, and step (c) comprises observing each of said cultures for an incidence of said result.

16. A cell bioassay according to claim 1, wherein said fluid sample is prepared by a process comprising the steps of blending flesh from an animal with acetone and filtering the resulting mixture.

* * * * *